US009694155B2

(12) United States Patent
Panova et al.

(10) Patent No.: US 9,694,155 B2
(45) Date of Patent: Jul. 4, 2017

(54) ADJUVANT METHOD FOR THE INTERFACE OF PSYCHOSOMATIC APPROACHES AND TECHNOLOGY FOR IMPROVING MEDICAL OUTCOMES

(71) Applicants: Juliana Stoianova Panova, Arlington Heights, IL (US); Joel Daniel Marcus, Mandeville, LA (US); Tayana Borisova Panova, Arlington Heights, IL (US)

(72) Inventors: Juliana Stoianova Panova, Arlington Heights, IL (US); Joel Daniel Marcus, Mandeville, LA (US); Tayana Borisova Panova, Arlington Heights, IL (US)

( * ) Notice: Subject to any disclaimer, the term of this patent is extended or adjusted under 35 U.S.C. 154(b) by 148 days.

(21) Appl. No.: 14/574,229

(22) Filed: Dec. 17, 2014

(65) Prior Publication Data
US 2015/0174362 A1 Jun. 25, 2015

Related U.S. Application Data
(60) Provisional application No. 61/917,335, filed on Dec. 17, 2013.

(51) Int. Cl.
*A61M 21/00* (2006.01)
*A61M 21/02* (2006.01)
(Continued)

(52) U.S. Cl.
CPC ............ *A61M 21/02* (2013.01); *A61B 5/165* (2013.01); *A61B 5/486* (2013.01);
(Continued)

(58) Field of Classification Search
CPC ..... G06B 19/00; G06F 3/011; G06F 19/3481; A61M 21/02; A61M 2021/0011; A61B 5/165
See application file for complete search history.

(56) References Cited

U.S. PATENT DOCUMENTS 5,546,943 A    8/1996  Gould
5,725,472 A *  3/1998  Weathers .......... A61M 21/0094
                                              128/905
(Continued)

FOREIGN PATENT DOCUMENTS

WO      2014124002      8/2014

OTHER PUBLICATIONS

Gallagher, G., Rae, C. P., & Kinsella, J. (2000). Treatment of pain in severe burns. American Journal of Clinical Dermatology, 1(6), 329-335.
(Continued)

*Primary Examiner* — Kristen Matter
(74) *Attorney, Agent, or Firm* — Stephen T. Scherrer; Monique A. Morneault; Scherrer Patent & Trademark Law, P.C.

(57) ABSTRACT

A method to induce an immediate psychosomatic change in a patient optimal for a particular medical procedure, is provided. The method uses a brain-computer interface integrating a loop of biofeedback and neurofeedback components, interactive, immersive, 3D virtual reality (VR) modules utilizing hypnotic or guided-response, learning, placebo and experience-ratification principles. The method will differentiate between low and high hypnotizable patients as well their specific abilities and limitations by their distinct brain patterns and will deliver VR output content appropriate for the current and targeted psychosomatic state of the patient, needs, and stage of a particular medical procedure thus being applicable to any medical patient regardless of abilities. The device will continuously measure the patient's physiological markers and will customize the intensity, order, timing, and content of the output "dose." The method is designed to be quickly implemented, entertaining and (Continued)

minimally obtrusive to distressed medical patients and medical settings.

12 Claims, 1 Drawing Sheet

(51) Int. Cl.
    A61B 5/16    (2006.01)
    A61B 5/00    (2006.01)
    G06F 19/00    (2011.01)
    G09B 19/00    (2006.01)

(52) U.S. Cl.
    CPC ... *G06F 19/3481* (2013.01); *A61M 2021/005* (2013.01); *A61M 2021/0011* (2013.01); *A61M 2021/0016* (2013.01); *A61M 2021/0022* (2013.01); *A61M 2021/0027* (2013.01); *A61M 2205/3306* (2013.01); *A61M 2230/06* (2013.01); *A61M 2230/10* (2013.01); *A61M 2230/63* (2013.01); *A61M 2230/65* (2013.01); *G09B 19/00* (2013.01)

(56) References Cited

U.S. PATENT DOCUMENTS

| | | | |
|---|---|---|---|
| 6,425,764 B1* | 7/2002 | Lamson | A61M 21/00 434/236 |
| 7,946,974 B2 | 5/2011 | Lordereau | |
| 8,517,912 B2 | 8/2013 | Clare | |
| 2002/0128540 A1 | 9/2002 | Kim et al. | |
| 2010/0010289 A1* | 1/2010 | Clare | A61M 21/00 600/27 |
| 2011/0213197 A1* | 9/2011 | Robertson | A61B 5/486 600/27 |

OTHER PUBLICATIONS

Spiegel, R. B. (2011). The Integration of Heart-Centered Hypnotherapy and Targeted Medical Hypnosis in the Surgical/Emergency Medicine Milieu. Journal of Heart-Centered Therapies, 14(2), 87-106.
Calipel, S., Lucaspolomeni, M., Wodey, E., & Ecoffey, C. (2005). Premedication in children: Hypnosis versus midazolam. Pediatric Anesthesia, 15(4), 275-281.
Butler, L. D., Symons, B. K., Henderson, S. L., Shortlifle, L. D., Spiegel, D. (2005). Hypnosis reduces distress and duration of an invasive medical procedure for children. Pediatrics, 115(1), e77-e85.
Lobe, T. E. (2006). Perioperative hypnosis reduces hospitalization in patients undergoing the Nuss procedure for pectus excavatum. Journal of Laparoendoscopic & Advanced Surgical Techniques, 16(6), 639-642.
Cowan, G. S., Jr., et al. (2001). Assessment of the effects of a taped cognitive behavior message on postoperative complications (therapeutic suggestions under anesthesia). Obesity Surgery, 11(5), 589-593.
Montgomery, G.H., DuHamel, K.N., & Redd, W.H. (2000). A meta-analysis of hypnotically induced analgesia: How effective is hypnosis? International Journal of Clinical and Experimental Hypnosis, 48, 138-153.
Patterson D.R., Jensen M. (2003). Hypnosis and clinical pain. Psychological Bulletin. 129(4):495-521.
Montgomery, G. H., David, D., Winkel, G., Silverstein, J. H., Bovbjerg, D. H. (2002). The Effectiveness of Adjunctive Hypnosis with Surgical Patients: A Meta-Analysis. Anesthesia & Analgesia. 94(6), 1639-1645.
Heap, M., Brown, R. J., Oakley, D. A. (2004). The Highly Hypnotizable Person: Theoretical, Experimental, and Clinical Issues. Psychology Press.

Hoeft, F., Gabrieli, J. D. E., Whitfield-Gabrieli, S., Haas, B. W., Bammer, R., Menon, V., Spiegel, D. (2012). Functional Brain Basis of Hypnotizability. Arch Gen Psychiatry. 69(10):1064-1072.
Vanhaudenhuyse A, Boly M, Balteau E, Schnakers C, Moonen G, Luxen A, Lamy M, Degueldre C, Brichant JF, Maquet P, Laureys S, Faymonville ME. (2009). Pain and non-pain processing during hypnosis: a thulium-YAG event-related fMRI study. Neuroimage. 47(3):1047-1054.
Gruzelier, J. (1998). a working model of the neurophysiology of hypnosis: a review of evidence. Contemporary Hypnosis, 15(1), 3-21.
John H. Gruzelier (2006). Frontal functions, connectivity and neural efficiency underpinning hypnosis and hypnotic susceptibility. Contemp. Hypnosis, 23(1): 15-32.
McClain-Furmanski, D., Horton, J. E., & Crawford, H. J. (1999). Inhibition of pain: Effects on somatosensory event-related potentials during hypnotic analgesia in high but not low hypnotizable persons. Presented at Cognitive Neuroscience Society annual meeting, Washington, DC.
Gruzelier J. H., Brow T. D., Perry A., Rhonder J., Thomas M. (1984). Hypnotic susceptibility: A lateral predisposition and altered cerebral asymmetry under hypnosis. International Journal of Psychophysiology; 2: 137-139.
McCormack K, Gruzelier J.H., (1993) Cerebral asymmetry and hypnosis: a signal detection analysis of divided visual field stimulation. Journal of Abnormal Psychology, 102: 352-7.
Jutai J., Gruzelier J.H., Golds J., Thomas M. (1993) Bilateral auditory-evoked potentials in conditions of hypnosis and focused attention. International Journal of Psychophysiology 15: 167-76.
Crawford H. J., Clarke S. W., Kitner-Triolo M. (1996). Self-generated happy and sad emotions in low and highly hypnotizable persons during waking and hypnosis: laterality and regional EEG activity differences. International Journal of Psychophysiology. 24(3):239-66.
Karlin, R., Morgan, D., & Goldstein, L. (1980). Hypnotic analgesia: A preliminary investigation of quantitated hemispheric electroencephalographic and attentional correlates. Journal of Abnormal Psychology, 89, 591-594.
Crawford, H.J., (1990). Cognitive and psychophysiological correlates of hypnosis. 47-54. In M. L. Fass & D. Brown (Eds.), Creative mastery in hypnosis and hypnoanalysis: A festschrift for Erica Fromm. Hillsdale, New Jersey: Lawrence Erlbaum Associates.
Gruzelier J.H. (1990): Neuropsychological investigations of hypnosis: Cerebral laterality and beyond. In Hypnosis: Theory, Research and Clinical Practice; Van Dyck R, Spinhoven Ph, Van der Does AJW, (eds) Free University Press: 38-51.
Tebēcis A.K., Provins KA., Fambach R. W., Pentony P. (1975). Hypnosis and the EEG. A quantitative investigation. J Nerv Ment Dis. 161(1):1-17.
Graffin N.F., Ray W.J., Lundy R. (1995). EEG concomitants of hypnosis and hypnotic susceptibility. Journal of Abnormal Psychology. 104(1). 123-131.
Sabourin, M.E., Cutcomb, S. D., Crawford, H. J., Pribram, K. (1990). EEG correlates of hypnotic susceptibility and hypnotic trance: spectral analysis and coherence. International Journal of Psychophysiology. 10 (2). 125-142.
Hammond, C. (2005). EEG Patterns and Hypnotizability. Biofeedback. 35-37.
Falkenstein M., Hohnbein J., Hoorman J., Blanke L. (1990). Effects of errors in choice reaction timetasks on the ERP under focussed and divided attention. Psychophysiological Brain Research. Tilburg: Tilburg University Press. 192-195.
Gehring W.J., Goss B., Coles M.G.H., Meyer D.E., Donchin E. A neural system for error detection and compensation. Psychological Science 1993;4: 385-39.
Cardena E., Terhune D. (2009). A note of caution on the Waterloo-Stanford Group Scale of hypnotic susceptibility: a brief communication. Int J Clin Exp Hypn, 57(2):222-6.
Baghdadi, G., Nasrabadi, A. M., (2012). Comparison of different EEG features in estimation of hypnosis susceptibility level. Computers in Biology and Medicine. 42(5), 590-597.

(56) References Cited

OTHER PUBLICATIONS

Greenberg, R.P., Bornstein, R.F., Greenberg, M.D., & Fisher, S. (1992). A meta-analysis of antidepressant outcome under "blinder" conditions. Journal of Consulting and Clinical Psychology, 60(5), 664-669; discussion 670-677.

Greenberg, R.P., Bornstein, R.F., Zborowski, M.J., Fisher, S., & Greenberg, M.D. (1994). A meta-analysis of fluoxetine outcome in the treatment of depression. Journal of Nervous and Mental Disease, 182(10), 547-551.

Greenberg, R.P., & Fisher, S. (1989). Examining antidepressant effectiveness: Findings, ambiguities, and some vexing puzzles. Hillsdale, NJ: Erlbaum.

Greenberg, R.P., & Fisher, S. (1997). Mood-mending medicines: Probing drug, psychotherapy, and placebo solutions. In S. Fisher & R.P. Greenberg (Eds.), From placebo to panacea: Putting psychiatric drugs to the test (pp. 115-172). New York: Wiley.

Kirsch, I., Moore, T.J., Scoboria, A., & Nicholls, S.S. (2002). The emperor's new drugs: An analysis of antidepressant medication data submitted to the U.S. Food and Drug Administration. Prevention & Treatment, 5(23).

Wagner, M.T., & Khanna, P. (1986). A neuropsychological model of hypnosis. International Journal of Psychosomatics, 33(3), 26-28.

Raz, A. (2007). Hypnobo: perspectives on hypnosis and placebo. American Journal of Clinical Psychology. 50(1), 29-36.

Amanzio, M. & Benedetti, F. (1999). Neuropharmacological dissection of placebo analgesia: Expectation-activated opioid systems versus conditioning-activated specific subsystems. The Journal of Neuroscience, 19(1), 484-494.

Bingel, U., Lorenz, J., Schoell, E., Weiller, C. & Büchel, C. (2006). Mechanisms of placebo analgesia: rACC recruitment of a subcortical antinociceptive network. Pain, 120(1-2), 8-15.

Vase, L., Petersen, G. L., Riley, J. L. & Price, D. D. (2009). Factors contributing to large analgesic effects in placebo mechanism studies conducted between 2002 and 2007. Pain, 145(1), 36-44.

Wager, T.D., Rilling, J.K., Smith, E.E., Sokolik, A., Casey, K.L., Davidson, R.J., Kosslyn, S.M., Rose, R.M., Cohen, J.D. (2004). Placebo-induced changes in fMRI in the anticipation and experience of pain. Science, 303(5661), 1162-1167.

Kirjanen, S. (2012). Brain activity during pain relief using hypnosis and placebo treatments: a literature review. Journal of European Psychology Students. vol. 3.

Benham, G., Bowers, S., Nash, M., & Muenchen, R. (1998). Self-fulfilling prophecy and hypnotic response are not the same thing. Journal of Personality and Social Psychology, 75(6), 1604-1613.

Kirsch, I., & Wickless, C. (1989). The effects of verbal and experiential expectancy manipulations on hypnotic susceptibility. Journal of Personality and Social Psychology, 57, 762-768.

Kirsch, I., Wickless, C., & Moffitt, K.H. (1999). Expectancy and suggestibility: Are the effects of environmental enhancement due to detection? International Journal of Clinical and Experimental Hypnosis, 47(1), 40-45.

Price, D.D., & Barrell, J.J. (2000). Mechanisms of analgesia produced by hypnosis and placebo suggestions. Progress in Brain Research, 122, 255-271.

Batty, M.J., Bonnington, S. Tang,B.K. Hawken, M.B. Gruzelier, J.H. (2006), Relaxation strategies and enhancement of hypnotic susceptibility: EEG neurofeedback, progressive muscle relaxation and self-hypnosis. Brain Research Bulletin, 71, 83-90.

Hammond, C. (1990). Handbook of Hypnotic Suggestions and Metaphors. The American Society of Clinical Hypnosis. New York: Norton and Company, Ltd.

Johnston, M. (1988). Impending surgery. In S. Fisher & J. Reason (Eds.) Handbook of life stress, cognition, and health (pp. 79-100). New York: Wiley.

Mathews, A., & Ridgeway, V. (1981). Personality and surgical recovery: A review. British Journal of Clinical Psychology, 20, 243-260.

Van den Brink, H., VanWijk, M., Bijlsma, J. (1992). Influence of steroid hormones on proliferation of peripheral blood mononuclear cells in patients with rheumatoid arthritis. British Journal of Rheumatology. 31(10), 663-667.

Meyerhoff, J.L., Oleshansky, M.A., Kalogeras, K.T., Mougey, E.H., Chrousus, G.P., Graner, L.G. (1990). Neuroendocrine responses to emotional stress: possible interactions between circulating factors and anterior pituitary hormone release. Circulating Regulatory Factors and Neuroendocrine Function, Advantages in Experimental Medicine and Biology. 274, 91-111.

Sternberg, E.M., Crousos, G.P., Wilder, R.L., Gold, P.W. (1992). The stress response and the regulation of inflammatory disease. Annals of Internal Medicine. 117(10), 854-866.

Egbert, L.D., Battit, G.E., Welch, C.E., & Barlett, M.K. (1964). Reduction of postoperative pain by encouragement and instruction of patients. New England Journal of Medicine, 270, 825-827.

Contrada, R. J., Leventhal, E. A., & Anderson, J. R. (1994). Psychological preparation for surgery: Marshaling Individual and social resources to optimize self-regulation. In S. Maes, H. Leventhal, & M. Johnson (Eds.), International Review of Health Psychology, vol. 3, 219-266. New York: Wiley.

Devine, E. (1992). Effects of psychoeducational care for adult surgical patients: A meta-analysis of 191 studies. Patient Education and Counseling, 19, 129-142.

Gil, K. M. (1984). Coping effectively with invasive medical procedures: A descriptive model Clinical Psychology Review, 4, 339-362.

Johnston, M., Vogele, C. (1993). Benefits of psychological preparation for surgery: A meta-analysis. Annals of Behavioral Medicine, 15, 245-256.

Johnston, M., Wallace, L (Eds.). (1990). Stress and medical procedures. Oxford, England: Oxford University Press, p. 184.

Mumford, E., Schlesinger, H. J., Glass, G. V. (1982). The effect of psychological intervention on recovery from surgery and heart attacks: An analysis of the literature. American Journal of Public Health, 72, 141-151.

Suls, J., Wan, C. K. (1989). Effects of sensory and procedural information on coping with stressful medical procedures and pain: A meta-analysis. Journal of Consulting and Clinical Psychology, 57, 372-379.

Kiecolt-Glaser, J. K., Page, G., Marucha, P.T., MacCallum, R. C., Glaser, R. (1998); Psychological Influences on Surgical Recovery. Perspectives From Psychoneuroimmunology. November; American Psychologist.

Abbott, J., Abbott, P. (1995). Psychological and cardiovascular predictors of anaesthesia induction, operative and postoperative complications in minor gynecological surgery. British Journal of Clinical Psychology, 34, 613-625.

Greene, P. G., Zeichner, A., Roberts, N. L., Callahan, E. J., & Granados, J.L. (1989). Preparation for cesarean delivery: A mutticompouent analysis of treatment outcome. Journal of Consulting and Clinical Psychology, 57, 484-487.

Markland, D., & Hardy, L. (1993). Anxiety, relaxation, and anesthesia for day-case surgery. British Journal of Clinical Psychology, 32, 493-504.

Scheier, M. E., Matthews, K.A., Owens, J. E, Magovem, G.J., Sr.,Lefebvre, R. C., Abbott, R. A., & Carver, C. S. (1989). Dispositional optimism and recovery from coronary artery bypass surgery: The beneficial effects on physical and psychological well-being. Journal of Personality and Social Psychology, 57, 1024-1040.

Liu, R., Barry, J. E. S., & Weinman, J. (1994). Effect of background stress on postoperative recovery. Anaesthesia, 49, 382-386.

Ewin, D. (1986). The effect of hypnosis and mind set on burns. Psychiatric Annals, 16, 115-118. Experimental Hypnosis. 56(4): 451-462.

Ben Eliyahu, S. Page, G.G., Yirmiya, R., Shakhar, G. (1999). Evidence that stress and surgical interventions promote tumor development by suppressing natural killer cell activity. International Journal of Cancer, 80(6), 880-888.

Ben Eliyahu, S. (2003). The promotion of tumor metastasis by surgery and stress: immunological basis and implications for psychoneuroimmunology. Brain, Behavior and Immunity, Feb;17 Suppl 1:S27-36.

(56) References Cited

OTHER PUBLICATIONS

Neeman, E., Zmora, O., Ben-Eliyahu, S. (2012). A new approach to reducing postsurgical cancer recurrence: perioperative targeting of catecholamines and prostaglandins. Clinical Cancer Research, 18(18), 4895-902.

Neeman, E., Ben-Eliyahu, S. (2013). Surgery and stress promote cancer metastasis: new outlooks on perioperative mediating mechanisms and immune involvement. Brain, Behavior and Immunity. Suppl:S, 32-40.

Sulea, C., Soomro, A., Boyd, C., Wiederhold, B. K. (2014). Pain management in virtual reality: a comprehensive research chart. Cyberpsychology, Behavior, and Social Networking, 17(6), 402-413.

Hoffman, H. G., Chambers, G. T., Meyer III, W. J., Arceneaux, L. L., Russel, W. J., Seibel, E J., Richards, T. L., Sharar, S. R., Patterson, D. R. (2011). Virtual reality as an adjunctive non-pharmacologic analgesic for acute burn pain during medical procedures. Annals of Behavioral Medicine, 41(2), 183-191.

Hoffman H. G., Meyer III W. J., Ramirez M., Roberts L., Seibel E. J., Atzori B., Sharar S. R., and Patterson D. R. (2014). Feasibility of articulated arm mounted oculus rift virtual reality goggles for adjunctive pain control during occupational therapy in pediatric burn patients. Cyberpsychology, Behavior, and Social Networking, 17(6), 397-401.

Maani, C., Hoffman, H. G., DeSocio, P. A., (2008). Pain control during wound care for combat-related burn injuries using custom articulated arm mounted virtual reality goggles. Journal of CyberTherapy and Rehabilitation, 1:193-198.

Flores A., Hoffman H. G., Russell W., (2008). Longer, multiple virtual reality pain distraction treatments of Hispanic and Caucasian children with large severe burns. CyberTherapy Conference. San Diego, CA.

Sharar, S. R., Carrougher, G. J., Nakamura, D., Hoffman, H. G., Blough, D. K., Patterson, D. R. (2007). Factors influencing the efficacy of virtual reality distraction analgesia during postburn physical therapy: preliminary results from 3 ongoing studies. Archives of Physical Medicine & Rehabilitation, 88(12), s43-s49.

Eccleston, C., Crombez, G. (1999). Pain demands attention: a cognitive-affective model of the interruptive function of pain. Psychological Bulletin, 125:356-366.

Hilgard, E. R. (1965). Hypnotic susceptibility. New York: Harcourt, Brace & World.

Hoffman H.G., Richards T.L., Bills A.R., (2006). Using FMRI to study the neural correlates of virtual reality analgesia. CNS Spectrums 11:45-51.

Patterson, D. R.; Hoffman, H. G.; Palacios, A. Garcia; Jensen, M. J. (2006). Analgesic effects of posthypnotic suggestions and virtual reality distraction on thermal pain. Journal of Abnormal Psychology, vol. 115(4). 834-841.

Spiegel H., Aronson M., Fleiss J. L., Haber J. (1976). Psychometric analysis of the Hypnotic Induction Profile. Int J Clin Exp Hypn. 24(3):300-315.

Hammond, C., Novian, A. (2014). The ISNR Comprehensive Bibliography of Neurofeedback in Scholarly Articles. Retrieved from: http://www.isnr.net/resources/comprehensive-bibliography.cfm.

Lang E.V., Berbaum K.S., Faintuch S., Hatsiopoulou O., Halsey N., Li X., Berbaum M. L., Laser E., Baum J. (2006). Adjunctive self-hypnotic relaxation for outpatient medical procedures: a prospective randomized trial with women undergoing large core breast biopsy. Pain.126(1-3):155-164.

Lang E.V., Benotsch E.G., Fick L.J., Lutgendorf S., Berbaum M.L., Berbaum K.S., Logan H., Spiegel D. (2000). Adjunctive non-pharmacological analgesia for invasive medical procedures: a randomised trial. 355(9214):1486-1490.

Montgomery G.H.,, Bovbjerg D.H., Schnur J.B., David D., Goldfarb A., Weitz C.R., Schechter C., Graff-Zivin J., Tatrow K., Price D.D., Silverstein J.H. (2007). A randomized clinical trial of a brief hypnosis intervention to control side effects in breast surgery patients. J Natl Cancer Inst. 99(17):1304-1312.

Lee J.S., Spiegel D., Kim S.B., Lee J.H., Kim S.I., Yang B.H., Choi J.H., Kho Y.C., Nam J.H. (2007). Fractal analysis of EEG in hypnosis and its relationship with hypnotizability. Int J Clin Exp Hypn. 55(1):14-31.

Colgan S.M., Faragher E.B., Whorwell P.J. (1988). Controlled trial of hypnotherapy in relapse prevention of duodenal ulceration. Lancet. 1(8598):1299-1300.

Hoffman, H. G., Chambers, G. T., Meyer III, W. J., Arceneaux, L. L., Russel, W. J., Seibel, E. J., Richards, T. L., Sharar, S. R., Patterson, D. R. (2011). Virtual reality as an adjunctive non-pharmacologic analgesic for acute burn pain during medical procedures. Annals of Behavioral Medicine, 41(2), 183-191.

Askay, S. W., Patterson, D. R., & Sharar, S. R. (2009). Virtual reality hypnosis. Contemporary Hypnosis (John Wiley & Sons, Inc.), 26(1), 40-47.

* cited by examiner

ADJUVANT METHOD FOR THE INTERFACE OF PSYCHOSOMATIC APPROACHES AND TECHNOLOGY FOR IMPROVING MEDICAL OUTCOMES

CROSS-REFERENCES TO RELATED APPLICATION

This application claims the benefit of PA No. 61/917,335, EFS ID 17689868, filed 2013, Dec. 17 by Juliana Panova, Joel Marcus

FIELD OF THE INVENTION

The present invention relates to a method for an immediate change of psychosomatic states in patients via a medical device by integrating psychosomatic approaches and immersive virtual reality. In particular, this invention relates to a method for reliably achieving the optimal psychosomatic state for the specific current needs of medical patients via a medical device utilizing brain-computer interface that integrates immersive, interactive virtual reality with bio- and neurofeedback and hypnotic or guided modules. Embodiments of the invention can be used in medical, psychiatry, psychotherapy, and self-help fields.

BACKGROUND OF THE INVENTION

Prior Art

The following is a tabulation of some prior art that presently appears relevant:

U.S. Patents

| Pat. No. | Kind Code | Issue Date | Patentee |
|---|---|---|---|
| 6,425,764 | B1 | 30 Jul. 2002 | Lamson |
| 7,946,974 | B2 | 24 May 2011 | Lordereau |
| 5,546,943 | A | 20 Aug. 1996 | Gould |

U.S. Patent Application Publications

| Publication Nr. | Kind Code | Publ. Date | Applicant |
|---|---|---|---|
| 20020128540 | A1 | Sep. 12, 2002 | Kim et al. |
| 20110213197 | A1 | Sep. 1, 2011 | Robertson, Franza |
| 20100010289 | A1 | Jan. 14, 2010 | Clare |

Foreign Patent Documents

| Foreign Doc. Nr. | Cntry Code | Kind Code | Pub. Dt | App or Patentee |
|---|---|---|---|---|
| 2014124002 | WO | A1 | 14 Aug. 2014 | Rebstock et al. |

NONPATENT LITERATURE DOCUMENTS

Hoffman H. G., Meyer III W. J., Ramirez M., Roberts L., Seibel E. J., Atzori B., Sharar S. R., and Patterson D. R. (2014). Feasibility of articulated arm mounted oculus rift virtual reality goggles for adjunctive pain control during occupational therapy in pediatric burn patients. Cyberpsychology, Behavior, and Social Networking, 17(6), 397-401.

Hoffman, H. G., Chambers, G. T., Meyer III, W. J., Arceneaux, L. L., Russel, W. J., Seibel, E. J., Richards, T. L., Sharar, S. R., Patterson, D. R. (2011). Virtual reality as an adjunctive non-pharmacologic analgesic for acute burn pain during medical procedures. Annals of Behavioral Medicine, 41(2), 183-191.

Askay, S. W., Patterson, D. R., & Sharar, S. R. (2009). Virtual reality hypnosis. Contemporary Hypnosis (John Wiley & Sons, Inc.), 26(1), 40-47.

Kim and colleagues in US Pat. No. 20020128540 A1 describe a method of using virtual reality biofeedback as a treatment for attention deficit disorder (ADD). This method proposes using interactive virtual reality modules to replicate real world training exercises for concentration and attention control. It is not meant to be a method for alleviating distress, to be utilized in clinical settings, or to immediately change psychosomatic state. There is also no use of hypnosis at any point. It is designed to be an entertaining and interactive alternative to the more tedious traditional ADD feedback training.

Robertson and Franza in US Pat. No. US 20110213197 A1 describe a type of virtual reality facilitated brain training that allows patients to recreate certain situations in their real lives within a virtual realm and practice healthier patterns of behavior and thinking while engaging in therapeutic learning. The virtual reality world is meant to be a type of therapeutic arena where patients can customize the landscape and practice adaptive behaviors which can then be carried over into real life. It is designed to be an ongoing process that takes time to develop and benefit from, as patients need to furnish their virtual world and develop scripts to carry out within it, and is therefore an adjuvant to cognitive behavioral therapy (CBT) and imagery rehearsal therapy (IRT) and is not an appropriate tool for medical settings.

Gould in U.S. Pat. No. 5,546,943 A also utilizes principles of psychoneuroimmunology and virtual reality to enhance patient self-efficacy, but it is meant to be primarily a self-healing therapy, and is not meant to immediately alleviate a distressed psychosomatic state. Also, it relies on real images of the patient's body collected via MRI, CAT, PET, and NMR, all which are very expensive methods for gathering visual data. The authors admit this is the case and explain that the proposed treatment is therefore a way to re-use expensive data that would otherwise be discarded after one time use, therefore the method is primarily a proposal for recycling medical data in a productive fashion. Our method would not use real patient data as it is expensive and time-consuming to collect and incorporate in the software and also because it will be counterproductive for the treatment. Seeing their own damaged physiology will trigger said patients' attention back to the distressing reality and thus will augment patient distress and trauma.

Lamson in U.S. Pat. No. 6,425,764 B1 describes primarily a theoretical proposal for incorporating virtual reality into a wide variety of traditional therapies. The virtual reality is described as a medium that can allow patients to practice and experiment with certain novel behaviors and ways of thinking. It is not meant to be a method for immediately altering a distressed psychosomatic state or for preparing patients for invasive treatment, but rather as an adjuvant to traditional psychotherapy.

Lordereau in U.S. Pat. No. 7,946,974 B2 describes a method envisioned as an ongoing treatment for disorders such as chronic pain or neuro-degenerative disease that functions by gradually strengthening the immune system using a very specific virtual reality environment described in the patent. Said environment is described as a room filled with various changing colors of light and a stylized character in the middle meant to resemble the patient, thereby triggering a minor effect where the patient identifies with the character. The approach is more alternative/energy based and would likely not be very effective for patients skeptical of alternative treatments. It also does not utilize any hypnosis or neurofeedback principles, which are core components of our method.

Clare in U.S. Pat. No. 8,517,912 B2 describes a device that will control the administration of a hypnosis experience using feedback from the user. The goal of this device is to induce hypnosis and hypnosis is therefore the end goal, whereas in our embodiments hypnosis is one of a variety of means utilized to achieve the goal of disengaging patients from a current distressed state and preparing them to be receptive to induction of a change in psychosomatic state. In Clare's first stages, the device eases the patient into hypnosis by describing what is about to happen. The efficiency of our embodiments relies on the strong distraction and immersion effect of the initial stages, which must be conducted without an extensive lead in to be sufficiently disengaging from the state of distress. His device also relies on the patient's susceptibility to hypnosis to be effective, which makes such a device limiting for the general population where only 10-20% of people are considered to be highly hypnotizable. Also, if low hypnotizable patients are subjected to hypnosis they can become additionally aggravated and traumatized if the treatment does not work for them. In addition, relevant research indicates that low hypnotizable subjects may experience even higher level of neurological arousal during hypnosis. Our device will differentiate between high and low hypnotizable subjects thus customizing the sessions for the exact needs and abilities of any medical patient.

Rebstock and colleagues in WO Pat. No. 2014124002 describe a method for combining virtual reality and biofeedback to create customized game experiences for treatment of certain disorders such as chronic pain and for rehabilitation. The device does not utilize neurofeedback, biofeedback training, or hypnosis and is not intended to be used for immediate change of psychosomatic state in distressed patients.

The team of Patterson, Hoffman and colleagues has done a lot of research on virtual reality in clinical settings. They have shown how virtual reality can be used to grab patients' attention and distract them from painful procedures (2011, 2014) and have described methods for virtual reality facilitated hypnosis (2009). Their work is mostly on pain analgesia during the time of administration, does not aim to instill learning and a lasting change of psychosomatic state within the patient, and does not integrate interactive bio- and neurofeedback modules to sync the virtual reality with the patient's real time psychophysiological indicators.

BACKGROUND

A growing body of research demonstrates that the nervous, endocrine, and immune systems are complexly interrelated and that physical, environmental, and psychosocial stressors have a profound influence on the neuroendocrine-immune function. This means that the body's response to stressors, mediated by internal and external circumstances, can lead to significant immunosuppression and determine the body's responsiveness to treatment. Therefore, an intervention that lowers stress and prepares the patient's psychological and physical state to be optimally responsive to treatment, especially during the crucial window of opportunity (discussed below) would greatly improve treatment outcomes.

A number of studies have found that high preoperative anxiety or stress is predictive of poorer outcomes, including greater pain, increased level of postoperative infections and complications, longer hospital stays, and poorer treatment compliance (1, 2). Any significant stress, including the one induced by an acute or chronic disease, medical procedures, and surgery, activate the limbic-hypothalamic-pituitary-adrenal axis (LHPA). This results in an increased release of the adrenocorticotropic hormone (ACTH) and cortisol that are associated with immunosuppression, including decreased lymphocyte proliferation and natural killer (NK) cell cytotoxicity both in vitro and in vivo (3). Numerous studies have confirmed the existence of the complex feedback loop between the immune system and the central nervous system (CNS), in which the main role is played by the LHPA axis (4,5).

Starting with the early study of Egbert et al. (6) numerous studies (7, 8, 9, 10, 11, 12, 13) have found that some kind of preoperative intervention (even a short one) intended to alter the psychological state of the patient leads to a more beneficial outcome, namely decreased anxiety and stress, less postoperative complications, fewer hospital days, overall better treatment compliance, reduced perception of pain and decreased use of analgesics, and alterations in physiological indexes (14). Other studies have found that the preoperative mental state can significantly influence physiological state and responses during surgery (15, 16, 17, 18) and the rate of postsurgical recovery (19).

The timing of a psychosomatic intervention is also of vital importance. The changes and deterioration in the endocrine system progress with the increased physical and mental stressors involved in the disease progression and in invasive treatments especially those involving surgery. Therefore, there is a "window of opportunity" in which a proper and well-coordinated psychosomatic adjunct to the medical treatment will not only alleviate the burden of psychosocial stressors but will also assist in normalizing the neuroendocrine-immune parameters, thus improving the overall outcome.

In one groundbreaking study on this topic, Dr. Dabney Ewin (20), a surgeon working with burn patients, demonstrated how the hypnotic "hallucination" may create physiological change that alters the course and outcome in severe burn cases, especially if implemented in the immediate aftermath of the burn incident. He noted that the secondary release of histamines in response to the initial body damage is in fact responsible for much of the tissue damage resulting in blisters and swelling. He demonstrated that the physiology responded to hypnotic hallucinations of cool temperature thus minimizing the secondary response of histamine release resulting in less tissue damage and faster healing (20).

In a series of recent studies Ben-Eliyahu and colleagues (21, 22, 23, 24) demonstrated that there is a very sensitive and critical window before and immediately after cancer surgery that can determine future outbreaks of preexisting micrometastases and the initiation of new metastases. They found in animal and human studies that the presurgical stress causes excessive release of catecholamines and prostaglandins, which were shown to be prominent in facilitating cancer recurrence through their direct impact on the malignant tissue and through suppressing antimetastatic immunity. Their findings show that stress-induced suppression of NK activity is sufficient to cause enhanced tumor development.

These findings, among many others in an extensive field of research, illustrate the importance of addressing patients' psychosomatic states during medical treatment, especially during the critical window, in order to achieve optimal health outcome.

Any illness or pain condition as well as the ensuing treatment are usually perceived by the person as a victimizing event known to be an additional blow to the person's psyche and ability to recover. Although the research has clearly shown that adjusting the psychosomatic state of a patient is a necessity that should precede any intensive or invasive intervention in order to achieve the best outcome, an accurate psychosomatic diagnosis is difficult to be obtained even by a qualified mental health provider. This is because he/she relies heavily on patients' self-reports, which are known to be unreliable and often do not correspond well to their real physical/mental state. There are objective means to assist in the diagnostic process but healthcare providers cannot usually provide the time and resources necessary for psychological testing, fMRI, PET, EEG, ECG, etc. tests to keep up with the diagnostic changes. Also, there is still a significant lack of a fast, customized and reliable method that will immediately achieve the desired change in a patient's state. The main reason is that the existing psychosomatic interventions are not well coordinated with the ongoing state of the patient and as such are often untimely, not well matched, or not properly dosed, and therefore underachieve in the outcome of the treatment.

One psychosomatic treatment method which has drawn interest in recent years is the use of virtual reality (VR). Numerous studies have shown how VR can help significantly reduce pain, anxiety, and discomfort for patients with various conditions, with the greatest concentration of studies demonstrating VR's positive effects on burn pain, cancer pain, phantom limb pain, chronic pain, rehabilitation, and pain attenuation with various other causalities (25).

VR treatment involves using a VR device, such as goggles or a helmet that blocks out the patient's view of the hospital setting, to deliver computer-generated images via screens within the headgear to a patient who is experiencing significant pain, stress, or discomfort. The idea is to refocus the patient's attention from the aversive experiences of their treatment onto a perceptually pleasant alternative world (26). The VR headgear is attached to a computer using special software which uses 3D graphics to engage patients' attention by guiding them through a world full of various characters, landscapes, and activities.

Patients exposed to VR treatment consistently report feeling less pain, less time thinking about their pain, and even experiencing fun during painful treatments (27, 26, 28, 29, 30). The experience of pain arises from the neural processing of signals from pain receptors, which means that attentional resources play an important role in creating the subjective feeling of pain (31). VR engages a significant amount of these resources and therefore leaves less of them available to focus on pain. Scientists have used fMRI to observe whether the brain behaves differently when a patient is engaged in VR while being made to feel pain, and they have found is that along with a subjective rating of significantly less pain, objective measures of neural activity showed 50% or greater reductions in pain-related brain activity in the anterior cingulate cortex, insula, thalamus, the primary and the secondary somatosensory cortex (33).

The effectiveness of VR approach has been proven significant and generalizable. The scope of existing research shows that patients in VR treatments report experiencing an average of 35-50% less pain than patients being treated as usual (26). Research has also found that the analgesic effects of VR existed equally for people irrespective of age, sex, ethnicity (30) and hypnotizability (34), a neural characteristic which determines the effectiveness of hypnosis.

Although proven as effective in some instances and pain conditions shortcomings of VR approach used alone also limit its widespread use in medical settings. Some of its limitations include 1) Since its power is primarily in distraction, the alleviating effects are generally confined to the duration of the VR exposure. Therefore there is no accumulative, educational and learning effect manifested via changed expectations, health related abilities and attitudes or neurogenesis and brain plasticity that is observed in BFB and NFB and in hypnosis. 2) VR is applicable primarily for distraction from pain/discomfort and therefore of limited use in pre- and post- surgery and any other treatment that requires more holistic or continuous change of the patient's psychosomatic state. 3) The patient is a simple recipient of the VR stimuli and does not develop a sense of mastery or self-efficacy over their bodies, thus the method will not have a continuous and significant effect over the distressed psychosomatic state.

Another treatment method used to improve people's psychosomatic state is bio- and neurofeedback. Neurofeedback is the cognitive subdivision of biofeedback, which is the method of presenting an individual with real time data about their own body functions such as heart rate, skin conductance, body temperatures, etc. in order to help them better understand what their body is doing and make it possible for them to control otherwise involuntary bodily functions.

Neurofeedback engages the fundamental learning process of operant conditioning, whereby people act, observe the effects of their action, and then alter the action the next time around until they achieve a desired response. The "desired response" in the case of biofeedback is the alteration of certain physiological markers, whereas in neurofeedback it is the enhancement of certain brainwaves and reduction of others, depending on what brainwave patterns are deemed optimal for the given patient's needs and abilities. The neurofeedback device helps patients achieve this brainwave optimization by collecting data about users' brain function via electrodes attached to the scalp. The therapeutic goal is accomplished by reinforcing the expression of the desired brainwaves with some kind of visual or auditory cue until gradually, via the link between the internal feeling and the external reinforcing stimuli, the patient unconsciously begins learning how that brainwave "feels" and becomes able to achieve it more easily. Neurofeedback's healing effects on ADD/ADHD, addictive disorders, cognitive decline, anxiety, autism, depression, epilepsy, OCD, pain and headaches, PTSD, Schizophrenia, optimal functioning and many more have been extensively documented (36).

However, the premise of the bio-neurofeedback training includes a general lack of guidance in the process and is based on a "reward" system (achieving a set goal manifested in a form of a sound and/or simple animation) designed to reinforce the corresponding physiological changes. As such it relies on the patients' ability for insight what they need to do and ability for self-control and concentration, and therefore, despite the good success rate if used as intended, the process is long, repetitive, and boring, and as such has a high dropout rate and cannot be used successfully in immediate care.

Hypnosis is a proven effective treatment method for various disorders and conditions that has so far been underutilized in its clinical use. Hypnosis alters the psychosomatic state of the patient and can be used to guide the patient into a state optimally responsive to treatment. Hypnosis has been consistently proven as an effective method for easing pain and anxiety, altering somatic functions and leading to improved outcomes after surgery, radiology and chemotherapy treatments, and other invasive medical procedures and treatments (37, 38, 39, 40, 41). Medical hypnosis has also been shown to reduce intra-operative blood loss, hospital stay, and pain and to accelerate bone and wound healing (42, 43, 44, 45). It has been used as a successful adjunct to treatment in coronary bypass surgery, severe burn treatment, and emergency medicine as well (46, 47, 48, 49).

A study on how hypnosis affects children having surgery reported that there were half as many anxious children in the hypnosis group than in the control group preoperatively and half as many with behavior disorders postoperatively (50). Children experiencing the painful and fear-inducing voiding cystourethrography (VCUG) also showed less trauma and distress from the procedure and had significantly easier and shorter procedures (by as much as 14 minutes) than non-hypnosis group children (51). Research has shown that patients in the hypnosis group have hospital stays that are 1.6 to 2 days shorter than patients in the non-hypnosis group (52, 53). There has also been evidence that participants in hypnosis groups exhibit structural differences in healing after surgical procedures. A study by Ginandes et al. (44) showed that after a reduction mammaplasty, women in the hypnosis group showed significantly greater wound healing than the non-hypnosis group, 1 through 7 weeks post-procedure.

A meta-analysis of 18 studies of hypnotically induced analgesia reported that hypnotic analgesia is "a valid and reliable phenomenon" with 75% of the clinical and experimental subjects reporting reduction in both acute and chronic pain (54), a finding supported by Patterson and Jenson (55). Another meta-analyses on hypnosis utility with surgical patients found that patients taking part in hypnosis treatment had better outcomes than 89% of patients in control groups, with beneficial effects observed in measures of negative affect, pain, pain medication, physiological indicators, recovery, and treatment time (56).

Although hypnosis has proven to be a powerful treatment method for a broad spectrum of disorders, it is plagued by many shortcomings. Limitations include the therapists' variables—ability, training, consistency—environmental variables, and the usual lack of an observable/objective feedback if and when the patient is ready for the next step in induction. The patient's variables interfering with the intervention are lower hypnotizability, lack in cognitive abilities of visualization and concentration, heightened distressed state/distractibility, and general distrust of hypnosis.

The ability to engage, narrow, focus and sustain attention is essential for the ability to experience and benefit from hypnosis. A person's hypnotizability is the degree to which he or she is susceptible to hypnosis, therefore, identifying who is and is not hypnotizable early on in treatment is vital to choosing the appropriate psychosomatic intervention and maximizing its benefits. In the professional field it is considered that roughly only 10-15% of the population is highly hypnotizable and the rest are moderate to low on hypnotizability (32, 57).

Hypnotizability is manifested in several different factors, one being structurally. Hoeft and colleagues (58) reported that highly hypnotizable individuals showed greater functional connectivity between the left dorsolateral prefrontal cortex (DLPFC) and the dorsal anterior cingulate cortex (dACC), anterior insula, amygdala, and ventral striatum, which are regions active in the process of selective attention and conflict resolution. According to the authors, this suggests that differences in hypnotizability lead to different top-down modulation of perception during the hypnosis (58). Other studies support the finding that hypnotic analgesia is associated with reduced activity of the dACC (59).

Differences in the attention control system seems to be the primary factor determining hypnotizability. Gruzeler (60, 61) in his studies found that high hypnotizable subjects manifested selective inhibitory influences on attention with hypnosis whereas low hypnotizable subjects improved attentional performance as the induction progressed. According to McClain-Furmanski and colleagues, the successful inhibition of pain during hypnotic analgesia requires active inhibitory processes which are thought to work by reallocating thalamocortical activities so that pain does not reach conscious awareness. According to their research, they conclude that highly hypnotizable subjects are more capable of suppressing pain because they practice more effective use of their frontal attentional system (62).

Hypnosis involves a process of detaching from reality and suspending critical evaluation, giving up control and allowing oneself to follow the path laid by the hypnotist's suggestion. According to Dr. John Gruzelier, this process is called "letting go" and is demonstrated by "frontolimbic inhibitory processes with dissociative or uncoupling consequences, left-sided in particular, encompassing orbitofrontal and dorsolateral frontal regions and limbic structures such as the amygdala, hippocampus and cingulate" (61). According to him, this letting go stage is accompanied by a shift towards a right hemispheric preference in those individuals who become hypnotized.

The research with high and low hypnotizable subjects found evidence of a left hemispheric preference in high susceptible subjects at baseline (63; 60). After hypnotic induction an enhancement of right posterior processing was observed, but only in high hypnotizable subjects it was that strictly lateralized. Gruzelier and colleagues found that in medium hypnotizable subjects the processing was more "widely distributed to include a bilateral processing enhancement and was of lesser magnitude" (69).

A shift towards right hemispheric activity for highly hypnotizable subjects during hypnosis is supported by numerous other studies (66; 67; 61; 64; 65; 60). According to Crawford (68) in their study on hypnosis and pain perception, the shift to increased right hemisphere involvement during hypnosis may occur because of the imagery participants are required to engage in, which is considered to be a right hemisphere activity (69).

Hypnosis induction and differences in hypnotizability are also expressed in patients' brain wave patterns. There have been numerous studies exploring the differences in electroencephalography (EEG) expression in high versus low hypnotizable patients, as well as research on the somatosensory event-related potentials (SERP) topography of individuals who achieve the hypnotized state versus those who do not. It is well observed phenomenon that theta brain waves increase more or less in all subjects entering a relaxed state and hypnotic induction. However, studies have reported that highly hypnotizable subjects have a higher theta expression than low susceptible subjects in their waking state before hypnosis (70; 71; 72) and show significantly greater theta power than the low hypnotizable subjects during the hypnosis induction (70; 68; 72). In support of theta expression's relationship with hypnotizability, most children over 5 are highly hypnotizable until the ages of 13-14, which is also around the time that their dominant brain frequency switches from theta to alpha (73).

Researchers have also used event related potential (ERP) to explore the brain's reaction to hypnotic hallucination. Electrophysiological evidence has shown that following conflicting response/stimulus, a large negative going wave at about 100 ms (N100) is emitted. This is evidenced to be an error detection wave, which is not elicited following correct responses (74, 75). In their study Gruzelier and colleagues (61) in an auditory detection task found that N100 was augmented in highly hypnotizable subjects at baseline, which indicates involvement of focused attention process. At the same time N100 was minimal in low hypnotizable subject indicating more distracted state and failure to engage frontal attentional circuits. It is a very important finding that after hypnotic induction N100 was progressively attenuated in high hypnotizable subject indicating disengagement of frontal processes. At the same time N100 attention wave was progressively increased in low hypnotizable subjects indicating progressive engagement of attention.

Hypnotizability has traditionally been measured by clinical tests and interviews such as the Stanford Hypnotic Susceptibility Scale and the Waterloo-Stanford Group Scale of hypnotic susceptibility, but such tests have been shown to have concerning drawbacks (76) and are limited by their lack of objective measures. Some of the inherent shortcomings of these kinds of tests such as their time consuming nature, their susceptibility to the confounding factors of patients' subjective distortions and the hypnotizer's biases, and their potential to detract from the depth of hypnosis. To combat the concerns of traditional hypnotizability assessments, Baghdadi and Nasrabadi (77) proposed an alternative, objective EEG based method. They carried out brainwave decomposition of gathered data to determine which brain waves were most active in the different subjects during a hypnosis session, and applied statistical analyses to determine which of those collected measures were reliably associated with hypnotizability. Their finding support the previous research on the topic presented above; mainly, that higher theta activity and stronger right hemispherity are associated with more highly hypnotizable subjects. They found that the strongest predictors of hypnotizability were theta activity at C4 (the right central sensorimotor region of the brain) and right temporal activity at T6. A device that can measure these two EEG features would lead to a fast and reliable method for assessing hypnotizability.

Although the effectiveness of hypnosis is moderated by hypnotizability, the placebo effect is a widespread and well-known phenomenon that has been documented in various populations. Some studies have found that over 75% of the "therapeutic" effects of some psychotropic drugs are actually accounted for by the placebo effect (78, 79, 80, 81, 82, 83, 84). The placebo phenomenon occurs when an individual experiences a curative outcome from a particular treatment or medication even though the intervention is lacking an active ingredient. The placebo effect has been shown to change activation in the somatosensory cortex, insula, thalamus, ACC, prefrontal cortex, amygdala, hypothalamus, hippocampus, periaqueductal grey, and nucleus accumbens (review in 89). Placebo research has shown that if subjects have been assured before the "treatment" that it works, they will experience greater alleviation from the "treatment" (85, 86, 87, 88, 89).

The observable change in physical and/or mental state caused by the placebo effect is evidence that an individual's expectations have a powerful influence over their wellbeing. Both hypnosis and placebo function by acting on the patient's expectations (90, 91, 92, 84) and influence the prefrontal region of the brain which has been shown to change with the expectation of pain relief (88, 93, 84). Some researchers postulate that hypnosis also becomes more effective with time and exposure simply due to the patients' familiarization and growing trust of the hypnosis process which alters their expectations of its effectiveness (94). These expectations can be altered by means other than hypnosis for those who are low on hypnotizability, such as through trance/experience-ratification—that is the process of building self-efficacy and confidence in patients by demonstrating to them how their minds, attitudes, and intentions influence their bodies (95).

SUMMARY

In accordance with one embodiment, the present invention is a method for an immediate and continuous change of psychosomatic state in patients via a medical device, achieved by integrating psychosomatic approaches and immersive virtual reality in a way that they compensate for each other's limitations and augment each other's effectiveness, making such a method applicable and efficient to almost any patient regardless of the personal abilities, hypnotizabilty, neurological differences, nature and level of the distressed state, or medical treatment.

STATEMENTS OF INVENTION

Figure 1:
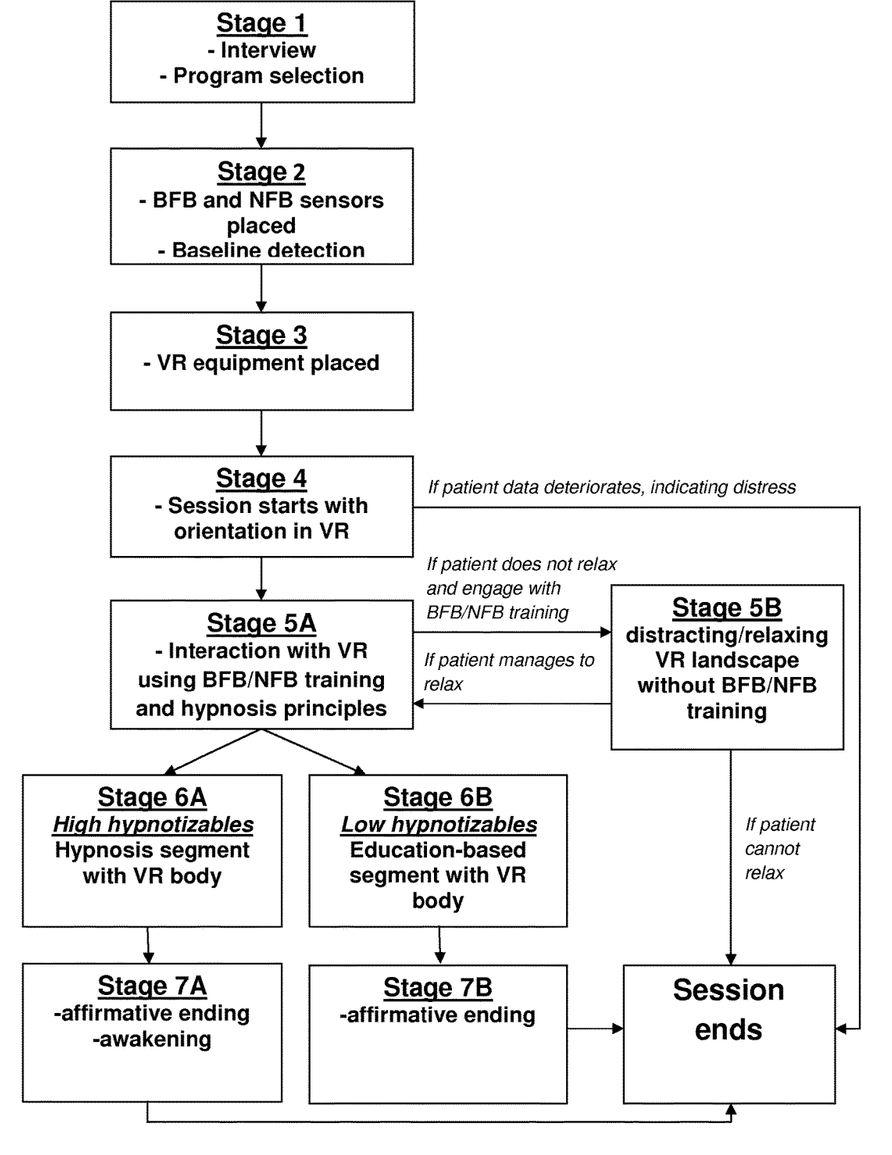
The FIGURE is a flowchart illustrating the order of the phases through which the patient will proceed during a session

All medical settings need a device that can deliver such an immediate intervention which is objectively and subjectively effective, observable, and measurable as a necessary adjunct to any treatment, especially those of an invasive nature and in immediate medical care. The relevant research has proven that there is a short window of opportunity where the stress hormones released during intensive and/or invasive medical procedures cause a significant immunosuppressant effect and further deterioration of patients' condition. Chronic or acute pain conditions and a distressed mental state due to various reasons have the same overall deteriorating effect on the body. Therefore it is medically relevant and vital that these distressed states are addressed in a timely manner and altered in order for any medical treatment or condition to be successful. None of the current methods and devices intended to influence psychosomatic states have the properties of achieving immediate change of said state and reprogramming said patient's mindset and physiology in real time in order to be optimally receptive to the treatment. These and other benefits of the method will become apparent in the ensuing description and accompanying diagram.

Some of the embodiments will utilize an integrative psychosomatic approach that will make such a device applicable and beneficial for almost any patient, irrespective of abilities, hypnotizabilty, neurological differences, and level of distressed state or possible medical treatment. In addition, the interactive component, that is, the patient's own contribution to the treatment, will increase the patient's sense of self-efficiency and control over his/her own life which will change expectations and condition the patient's neurological state to be optimally conducive for the rest of the medical treatment. Therefore, the implementation of such an adjuvant method which reliably alters the psychosomatic state along with its entertaining quality will significantly improve treatment compliance, as well as the course and outcome of any treatment.

According to one embodiment of the present invention, this is a method for a medical device for inducing immediate change of psychosomatic state of a medical patient in order to achieve more appropriate and conducive physiological state for a medical treatment. The method will be explained in accordance with one of the embodiments and the FIGURE.

A method for a medical device comprising a brain-computer interface that integrates a loop of biofeedback (BFB) and neurofeedback (NFB) components with interactive, immersive, 3D virtual reality (VR) modules and hypnosis and/or guided-response components. The device will differentiate between low and high hypnotizable patients and will deliver VR audio/video output segments that will be appropriate for the needed state of the patient, customized to their hypnotizability profile. The device will continuously monitor said patient's physiological markers and based on the input BFB and NFB data will customize the intensity, order, timing, and content of the output "dose" of the interactive, 3D VR multisensory induction content for immediate alteration of the psychosomatic state.

A device based on the proposed method is a necessary adjunct to any medical treatment, especially more invasive ones, because these types of treatments induce the highest levels of mental and physiological stress and the ensuing detrimental stress-triggered biochemistry within the patients. Highly distressed patients also often have a paradoxical reaction of enhanced sympathetic reaction and anxiety when they are asked to relax, if they are not prepared or do not feel capable of doing so. Therefore, initial multisensory virtual immersion is necessary to disengage the attentional network from the distressing thoughts and the medical environment and to redirect them to an immersive experience that will promote immediate relaxation and engagement of the parasympathetic branch of the autonomic nervous system.

Stage 1: A human operator collects data from the patient via a quick interview and/or a provided medical file to determine the patient's preferences and needed parameters, and enters the information into the device software. These preliminary questions may comprise, but are not limited to: said patient's gender; main medical problem and its location(s) in the body; associated medical treatment/procedure to be conducted; auditory impairment or language barrier; and appropriate and/or preferred set of virtual reality 3D environments. These parameters will be converged within the device software to customize a session for the current medical needs of said patient. A more prolonged interview or preliminary tests related to determining said patient suitability for a session with said device are not necessary and if done could have an adverse effect of inducing additional distress in said patient.

Stage 2: Said human operator places on said patient input sensors for the Biofeedback (BFB) and Nerofeedback (NFB) component of said device. Said sensors are comprised of the current most technologically advanced and unobtrusive sensors that are easy to place and use in order to obtain continuous data of real time physiological markers and brain waves of said patient. Currently, electroencephalography (EEG) headsets for NFB are developed and produced that can be instantly placed on the patient's scalp to measure brainwave activity with no additional preparation. They are comprised of semidry or dry sensors capable of measuring a plurality (9 or more) of positions on the scalp. The positions of interest in regard to brain mapping can comprise, but are not limited to, the frontal and temporal lobe of left and right hemispheres. Recent research on the matter has found that the strongest predictors of hypnotizability are theta activity at C4 (the right central sensorimotor region of the brain) and right temporal activity at T6. Said device can measure these two EEG features that allow for a fast and reliable method for assessing hypnotizability.

The input sensors placed on said patient may comprise but are not limited to measures of physiological parameters such as brainwave activity, galvanic skin response, heart rate, pupil dilation, eye and head tracking, motion and tactile control, even facial expression analysis and cognitive state. The input data of said patient's measured physiological markers during every session will be recorded, saved and can be displayed at any time as a numerical, graphical representation and/or graphical animation, illustrating in real time the change attained during a single session and/or the entire treatment.

At this stage a quick predetermined baseline of real time physiological data is obtained from said patient and stored in the memory of said device for comparison with normative data and said patient's previous data (if available), and to calculate a threshold as a treatment goal for the session. The goal of the treatment, via the output of the VR guided modules, is said patient to progress from the baseline brainwave frequency measured prior to a session at an awake state, to the frequency that is calculated by said device to be the achievable goal for the session. This frequency is determined by said patient's baseline, stated needs, continuous input of said patient's physiological markers indicating what type and amount of output segment said patient is ready to receive, as well as saved data from past sessions (if available). An option is provided for said operator to be able to manually enter and set a goal for the session.

Stage 3: Said operator places the 3D VR headset on said patient's head and starts a session as predetermined by the software specifications customized in the stage 1 and 2. The technology involved in this stage is comprised of means to provide a multisensory immersive experience to said patient. In order to make the VR experience more immersive and as such disengaging and distracting from the current state, the output component of the device may integrate a range of new technologies. It may comprise, but is not limited to, augmented reality, scent activators (currently emerging), and haptic technology (adding a sense of touch). The use of miniaturization technology will allow sensors to be portable and easy to place. Said patient will be fitted with a means for receiving the output module. It may include but is not limited to haptic glove(s) and a headset that will present the immersive 3D VR guided modules, which will use realistic animation or real world images and videos with sound and verbal instructions for hypnotic induction or relaxation directions.

Said device outputs a VR 3D, immersive, interactive, multisensory segment. It is designed to interfere with and disengage said patient's attentional network from his/her current attentional preoccupation, that is, said patient's distressed state and medical environment. This is accomplished by engaging as much as possible of the attentional brain network resources of said patient via immersing him/ her in a multisensory VR environment. Due to the limited attentional brain resource this will allow the distraction/disengagement of said patient from said environment, procedures, and distressing thoughts which are causing said patient further psychophysiolgal deterioration. As a result the sense of suffering, stress, and/or pain will be alleviated or at least significantly diminished which in return will diminish or cease the release of stress hormones and their effect and their immunosuppressant role on the entire body. The nature of said VR segment is desirable to be multisensory and immersive by engaging as many as possible of said patient's senses and associated brain resources but it should not be emotionally overloading. Therefore, said patient's acquired initial preferences for a relaxing environment need to be taken into account for customizing the session. Also, depending on said patient's physiological and/or mental distress, an output specifically needed and appropriate for said distress may be presented (e.g. a snow or cold/icy environment for burn patients).

Stage 4: Said device will allow a brief time period for orientation in the 3D VR immersive environment which is a different and engaging experience for said patient's senses. The duration of said period will be determined by the BFB and NFB input data. If said data does not deteriorate within a short predetermined time, indicating a more distressed state, and remains relatively stable or improves compared to the baseline and normative data, said device proceeds to the next stage. If the data notably deteriorates within predetermined limits the session will be terminated at this point automatically and an indicating signal will be presented for said operator. Also the time for that segment can be prolonged or shortened if necessary or desired via request of said patient or by said operator.

Stage 5A: A VR segment featuring a preselected natural environment will reflect visually the measures of said patient's current physiological state. (i.e. it may get gloomier, windy, cloudy, etc. to indicate current distress). Most of the VR interactive segments are designed as a distracting/entertaining manifestation of BFB and NFB component of said device, as the VR visual segments are corresponding to said patient's physiological markers. At that time a voice (or optionally subtitles for the auditory impaired) will start to guide said patient into a relaxed state, explaining how the VR environment will begin to reflect said patient's psychophysiological changes and become calmer as said patient relaxes. To keep the experience interactive and engaging, an animated object (i.e. a boat, a kite, balloon, flowers, animals, etc.) may be presented in the virtual reality landscape, which will move in tandem with the changes in said patient's physiological markers using BFB/NFB training principles. Reaching and maintaining a goal of a desired psychosomatic state will be rewarded by visual and auditory events such as calming the natural environment and moving the said object as desired.

Patients in medical settings who are dealing with intensive, invasive, medical care are very distressed and feel that they have lost ownership and control over their bodies and lives, which becomes a major component of their distressed state. To alleviate this accompanying distress and to regain hope, the patients need to regain some agency and control over their own state. Therefore Stage 5 serves not only as a distraction and relaxation stage but also as trance—or experience ratification—the phenomenon when patients manage to accomplish a change in their psychosomatic state by will, thereby changing their attitude and expectations about their participation in the treatment process. The patients will experience that they are capable of influencing the outcome of the procedure and will therefore achieve a feeling of self-efficacy. As a result, they will be conditioned neurologically to benefit optimally from the next session and/or from the medical procedure being assisted by said method.

Unlike it is in the BFB traditional training here the process will be guided by a calming voice similar to hypnotic inductions, without indicating that a hypnotic phenomenon is intended as a result. The reasoning is that a significant percentage of people are either not or think that they are not hypnotizable and/or do not believe in hypnosis. As result their negative expectations about hypnosis may have an adverse effect on the treatment success. The operant conditioning principle underlying BFB and NFB effectiveness will facilitate said patient's ability to become aware of and change his/her physiological state by watching the changes in the VR environment corresponding to their own state. Said stage may continue until a goal is reached and maintained within predetermined time or more if requested by said patient and/or specified by said operator.

Stage 5B: If said patient is not successful within a predetermined time period in interacting with the images on the screen, thereby indicating an insignificant change in the BFB/NFB markers, said device will switch to an automatic mode. The said mode will involve improving the condition in the VR environment automatically with a proper guidance for relaxation. It will also continue emitting the VR content without the interactive mode, for distracting and relaxing purposes, and will continue monitoring physiological markers within a predetermined time period. If said markers improve within a predetermined margin the device will return said patient to the interactive VR environment (moving an object via the BFB/NFB loop) and will continue the session as usual proceeding to the next stages. This alternative is needed in order to leave said patient with a positive mindset induced by guiding suggestion so that he can remain relaxed. The patient should not be left with a feeling that he has failed the task. As a result said patient will still have the benefit of the distracting and relaxing experience and additional possible placebo effect due to the positive experience.

If the input data deteriorates over a predetermined margin of physiological markers the session will be terminated automatically and an indicating signal will be emitted for said operator.

At the end of stage 5, said device will have gathered sufficient emitted brainwaves data (via EEG or other appropriate method) to compare with baseline and to determine if said patient is highly hypnotizable or not. Said patient will be considered by said device "highly" hypnotizable if said patient's brain wave data indicates several predetermined changes that my happen during this stage due to the induction of relaxation and "letting go" phenomenon indicating uncoupling of attentional resources from reality and switching them to the guided visual immersive experience. Said changes may be, but are not limited to, an EEG event of a significant switch to right hemispheric activity as measured at (but not limited to) brain placement T6 and combined with significantly increased Theta (4-7 Hz) brain wave emission measured (but not limited to) at brain placement C4. The research on the matter is still ongoing therefore any future findings in regard to any reliable and measurable physiological event that can serve as a determining index for hypnotizability may be utilized.

A "low" hypnotizable patient will be indicated if the expected above changes in brain waves for high hypnotizability do not occur within the predetermined markers, and/or if the EEG indicates more diffuse engagement of brain areas; and/or similar and continuous engagement of the left and right hemispheres.

Stage 6A: If the data from stage 5 indicates a "high" hypnotizable patient the device will continue with the next segment designed to utilize said patient's hypnotizability for an additional change of his/her psychosomatic state and/or prepare said patient for said medical procedure specified in phase 1. The stage begins with a statement and/or a visual summary for trance ratification—that is, affirmatively indicating said patient's ability to influence his/her own body by will as demonstrated in the previous phase. This will enhance said patient's trust in self and the treatment and will change positively his/her expectations that will further positively influence said patient's hypnotizability and engagement with the induction process. However, it is preferable that said device not to utilize words and expressions indicating hypnosis and hypnotic process to avoid a possible clash with a patient's belief system thereby impeding expectations and the therapeutic effect. The hypnotic principles and dynamic will be utilized in a guiding manner by said voice but will not be explicitly stated.

The statement/summary for trance ratification is followed by a 3D VR segment of a generic, stylized body image of the assigned gender in phase 1. The focus is gradually narrowed on a body location and/or medical procedure as specified in phase 1. Said location may be marked with a different color to stand out. The images of the particular organs and said location should be somewhat abstract or subtle. Explicit or real images of impaired body structures should be avoided so as not to evoke traumatic memories and anxiety-provoking thoughts in said patient which may adversely interfere with the ongoing therapeutic process.

Said device monitors physiological markers and if the patient maintains the desired level for hypnotic trance (as specified at Stage 5) the guiding voice starts to narrate a hypnotic induction about the needed changes and process that the patient will need to accomplish in order to achieve the desired outcome of the treatment. Said changes and processes are demonstrated taking place in the virtual reality as the animation of the body changes colors or structural features in the desired direction, thereby indicating an achievement of the goal in question. The segment is concluded with a posthypnotic suggestion about the desired changes and abilities that said patient may want/need to achieve.

Post hypnotic suggestions may require a cue to set off the outcome or new behavior. Said cue may be a time, an event, or expected daily routines/procedures. Post hypnotic suggestions can remain potentially active for many years. As long as the context and conditions are relevant, said patient will be able to respond to said post-hypnotic suggestion in the distant future without any conscious memory of it being given.

The goal of this stage is to induce an experience that will build a belief in said patient that he/she is not a victim but rather an active member of the medical team. Said patient may be instructed for (but not limited to) hypnotic anesthesia, or be instructed to detract blood from the area about to be operated, and/or to allow the immune cells to proliferate sufficiently and to rush to defend the body from the malignant pathogens, and so on. Via hypnotic induction and imagery said patient will be led through the process of altering said patient's body's state by using his mind. As a result of said hypnotic induction, visual images, and post-hypnotic suggestions, said patient will engage the necessary resources of the body for faster recovery during and post medical treatment.

If said device starts measuring more distressed physiological markers over a predetermined threshold, it will shorten and speed up the induction to an achieved goal (as predetermined by said patient's specifications) and will move to a stage 7A.

Stage 6B: If gathered data from stage 5 indicates a more relaxed state compared to said patient's baseline but that the patient is "low" on hypnotizability, said device will continue with the next VR segment customized for said patient's abilities. Said segment is designed to utilize said patient's more engaged attentional network at this stage for an additional change of said state and/or to prepare him/her for said medical procedure as specified in phase 1.

Said stage will also be effective in changing said patient's expectations for treatment and perception of their role in the treatment process, using principles of suggestion and learning. Therefore, consistent with research, expectations will play a significant role in said patient's ability to benefit from said method. Said patient's expectations can be altered by the alternative module 6B as in the hypnosis module 6A, but using slightly different means. By using educational principles and guided response instead of hypnotic induction, the device will once again engage the patient in a VR-facilitated familiarization with mind-body functioning and/or the medical procedures and said patient's vital role in it, thereby teaching them how they can regain power over their well-being.

The stage begins with a statement by a narrating voice and/or visual summary for experience ratification—that is, affirmatively indicating said patient's ability to influence his/her own body by will as demonstrated in the previous immersive and relaxation phase 5A. This will enhance said patient's trust and expectations, thus positively influencing further their suggestibility, immersion and engagement with the therapeutic process.

Said statement is followed by a VR animated segment of said body image discussed in 6A with the colors and location customized according to said patient's specifications. Said segment is accompanied by said voice that starts to narrate what said patient can accomplish by will in his/her own body in order to achieve the desired outcome. It is accompanied by an animated demonstration as the animation is changing colors or structure in the desired direction indicating achievement of the goal. In this phase the goal is to engage said patient's more focused attention and receptiveness resulting from the guided relaxed state (indicated by the relevant research) which is conducive to better learning and change of attitudes. Therefore the content of this VR visual segment will be designed according to educational principles. Said device monitors said markers, and if the patient maintains the desired predetermined level of relaxation said segment is concluded within a predetermined time with an affirmative statement by said voice for said patient's ability to be an efficient and important part in his/her own medical treatment and health as demonstrated by said patient's ability to change and improve of his/her current state. Said segment will also have an educative effect, thus changing said patient's expectations about treatment and outcome and as a result enhancing his/her suggestibility and hypnotizability, thereby having also a positive placebo effect.

If said device starts measuring more distressed physiological markers over a predetermined threshold, it will shorten and speed up the demonstration to an achieved goal as predetermined by patient's specifications and will move to stage 7B.

Stage 7A: Said patient of segment 6A is returned to said VR nature segment from the relaxed state at stage 5.

Selecting means in the device may select a segment from the recorded data that correspond to the most relaxed state recorded during the session, indicated by the physiological markers of said patient. An affirmative statement/image about said patient's successful session and increased ability to achieve his/her goal may conclude the session. A predetermined sign such as gradually increasing sound, a statement, or counting may be present to reawaken said patient from a hypnotic trance. The session ends.

Stage 7B: Said patient of segment 6B is returned to said VR nature segment from the relaxed state at stage 5. Selecting means in the device may select a segment from the recorded data that correspond to the most relaxed state indicated by recorded during the session physiological markers of said patient. An affirmative statement/image about said patient's successful session and increased ability to achieve his/her goal may conclude the session. The session ends.

If said device is used even a single time, the effects will decrease stress and distract from the negative experience during the critical window of opportunity around trauma or before, during and soon after an invasive medical procedure. This will allow for the more successful outcome of said medical procedure and faster healing due to the minimized effect of stress hormones and their immunosuppressive effect. Also, when used in the immediate treatment of burn victims it will minimize the effect of the secondary release of histamine responsible for deeper tissue damage and blisters. Therefore, distracting patients from the state of panic and stress, along with the process of trance-ratification and self-efficacy enhancement achieved via the BFB/NFB, learning and change of expectation phases, will lead to a psychosomatic state more receptive to treatment, and therefore will lead to improved outcomes.

When repeated use is possible, said method will utilize and augment the proven benefits of hypnosis and biofeedback as treatment approaches. As the relevant research indicates, a treatment implementing these approaches and achieving a continuous change of psychosomatic state will result in beneficial neurogenesis due to brain plasticity reflecting the new acquired abilities and different neurological reactivity. Said patient will learn to identify his distressing states and how to achieve, by will, a more conducive state for his health needs.

In another embodiment, when it is desired or needed, due to a language barrier or other reason, the above stages of the first embodiment may exclude the narrating guiding voice. In said embodiment the visual segments in stage 5 serve mostly as a BFB, NFB animation corresponding to the real-time measured physiological markers of said patient. The operant conditioning principle will be reinforced by said patient moving the said objects in said VR segments. It is desirable in said embodiment for haptic and/or other sensory technology to be utilized for assuring a multisensory immersive experience, considering the lack of auditory content.

In another embodiment, additional auditory technologies may be utilized for achieving higher suggestibility. Binaural beats involves technology presenting individual tones to each ear of a user. If one ear is presented with a steady tone of say 500 Hz and the other ear a steady tone of 510 Hz, the two tones combine in the brain. The difference of 10 Hz is perceived by the brain and is a proven to be very effective stimulus for brainwave training (e.g. Theta at 4 to 7 Hz). The frequency difference, when perceived by said patient's brain, is a binaural beat.

In another embodiment, double induction may be utilized in stages 5, 6 and/or 7 that involves playing two messages, at the same time, to separate ears. The premise is that the conscious mind tries to listen to one message, while the other goes directly into the subconscious mind, bypassing the cognitive filter. Thus it can circumvent some of said patient's disbeliefs or negative expectations.

In another embodiment additional visual technology may be utilized for achieving higher suggestibility. Subliminal messaging may be embedded in the visual segments. This involves short and very rapid messages or words that are played to said patient. The messages/words are so fast that the conscious mind does not register or filter them. The premise is that a person's unconscious mind recognizes the messages and the suggestions are embedded.

The proposed invention is a method, not a strict set of technological procedures therefore it is not limited to current technological advances, especially considering how rapidly the fields of virtual reality, neurogaming, and neurosciences are advancing. Therefore any new technology that emerges and provides means for effective immersive sensory engagement may serve as distraction means to disengage said patient from the current distressed state. Also, any means that provide effective ways for a person to interact with the multi-sensory output may be employed. The goal is to engage as much as possible of said patient's attentional network and sensory system in order to ensure faster and more effective change of said state, therefore any means that can do so optimally may be employed.

The output means of said device comprise an algorithm to execute a content selection, determining what segment should be output to correspond to the input BFB and EEG data and what segments should follow sequentially. Said means further comprise a text-to-speech engine designed to select text content from a plurality of stored text content data segments and convert it into an audio speech signal suitable for the particular input data and VR visual content.

Said device further comprises recording and storing means for recording and storing all activity in a session comprised of baseline data taken initially while no stimulus is presented at; input and output data, timing, most effective data segments, length and type of segments, and their sequential order. Said means may provide a full audit trail of every session.

Output means may include a microphone to enable said operator to output verbal content and an output channel that will allow said operator to output text-to-voice to said patient during a session.

The real-time outputting means comprises display means for a graphical representation of the input data to the sensory output device.

Another embodiment of the invention includes a game console configured to operate a handheld or hand-touch control, or any current innovation that is most conducive to the immersion goals of the device to operate objects in output interactive segments.

REFERENCES

1. Johnston, M. (1988). Impending surgery. In S. Fisher & J. Reason (Eds.) Handbook of life stress, cognition, and health (pp. 79-100). New York: Wiley
2. Mathews, A., & Ridgeway, V. (1981). Personality and surgical recovery: A review. British Journal of Clinical Psychology, 20, 243-260.
3. Van den Brink, H., VanWijk, M., Bijlsma, J. (1992). Influence of steroid hormones on proliferation of peripheral blood mononuclear cells in patients with rheumatoid arthritis. British Journal of Rheumatology. 31(10), 663-667.
4. Meyerhoff, J. L., Oleshansky, M. A., Kalogeras, K. T., Mougey, E. H., Chrousus, G. P., Graner, L. G. (1990). Neuroendocrine responses to emotional stress: possible interactions between circulating factors and anterior pituitary hormone release. Circulating Regulatory Factors and Neuroendocrine Function, Advantages in Experimental Medicine and Biology. 274, 91-111.
5. Sternberg, E. M., Crousos, G. P., Wilder, R. L., Gold, P. W. (1992). The stress response and the regulation of inflammatory disease. Annals of Internal Medicine. 117 (10), 854-866.
6. Egbert, L. D., Battit, G. E., Welch, C. E., & Barlett, M. K. (1964). Reduction of postoperative pain by encouragement and instruction of patients. New England Journal of Medicine, 270, 825-827.
7. Contrada, R. J., Leventhal, E. A., & Anderson, J. R. (1994). Psychological preparation for surgery: Marshaling individual and social resources to optimize self-regulation. In S. Maes, H. Leventhal, & M. Johnson (Eds.), International Review of Health Psychology, Vol. 3, 219-266. New York: Wiley.
8. Devine, E. (1992). Effects of psychoeducational care for adult surgical patients: A meta-analysis of 191 studies. Patient Education and Counseling, 19, 129-142.
9. Gil, K. M. (1984). Coping effectively with invasive medical procedures: A descriptive model. Clinical Psychology Review, 4, 339-362.
10. Johnston, M., Vogele, C. (1993). Benefits of psychological preparation for surgery: A meta-analysis. Annals of Behavioral Medicine, 15, 245-256.
11. Johnston, M., Wallace, L. (Eds.). (1990). Stress and medical procedures. Oxford, England: Oxford University Press, p 184.
12. Mumford, E., Schlesinger, H. J., Glass, G. V. (1982). The effect of psychological intervention on recovery from surgery and heart attacks: An analysis of the literature. American Journal of Public Health, 72, 141-151.
13. Suls, J., Wan, C. K. (1989). Effects of sensory and procedural information on coping with stressful medical procedures and pain: A meta-analysis. Journal of Consulting and Clinical Psychology, 57, 372-379.
14. Kiecolt-Glaser, J. K., Page, G., Marucha, P. T., MacCallum, R. C., Glaser, R. (1998); Psychological Influences on Surgical Recovery. Perspectives From Psychoneuroimmunology. November; American Psychologist.
15. Abbott, J., Abbott, P. (1995). Psychological and cardiovascular predictors of anaesthesia induction, operative and postoperative complications in minor gynecological surgery. British Journal of Clinical Psychology, 34, 613-625.
16. Greene, P. G., Zeichner, A., Roberts, N. L., Caltahan, E. J., & Granados, J. L. (1989). Preparation for cesarean delivery: A mutticompouent analysis of treatment outcome. Journal of Consulting and Clinical Psychology, 57, 484-487.
17. Markland, D., & Hardy, L. (1993). Anxiety, relaxation, and anesthesia for day-case surgery. British Journal of Clinical Psychology, 32, 493-504.
18. Scheier, M. E., Matthews, K. A., Owens, J. E, Magovern, G. J., Sr., Lefebvre, R. C., Abbott, R. A., & Carver, C. S. (1989). Dispositional optimism and recovery from coronary artery bypass surgery: The beneficial effects on physical and psychological well-being. Journal of Personality and Social Psychology, 57, 1024-1040.
19. Liu, R., Barry, J. E. S., & Weinman, J. (1994). Effect of background stress on postoperative recovery. Anaesthesia, 49, 382-386.
20. Ewin, D. (1986). The effect of hypnosis and mind set on burns. Psychiatric Annals, 16, 115-118. Experimental Hypnosis. 56(4): 451-462.
21. Ben Eliyahu, S. Page, G. G., Yirmiya, R., Shakhar, G. (1999). Evidence that stress and surgical interventions promote tumor development by suppressing natural killer cell activity. International Journal of Cancer, 80(6), 880-888.
22. Ben Eliyahu, S. (2003). The promotion of tumor metastasis by surgery and stress: immunological basis and implications for psychoneuroimmunology. Brain, Behavior and Immunity, February; 17 Suppl 1:S27-36.
23. Neeman, E., Zmora, O., Ben-Eliyahu, S. (2012). A new approach to reducing postsurgical cancer recurrence: perioperative targeting of catecholamines and prostaglandins. Clinical Cancer Research, 18(18), 4895-902.
24. Neeman, E., Ben-Eliyahu, S. (2013). Surgery and stress promote cancer metastasis: new outlooks on perioperative mediating mechanisms and immune involvement. Brain, Behavior and Immunity. Suppl:S, 32-40.
25. Sulea, C., Soomro, A., Boyd, C., Wiederhold, B. K. (2014). Pain management in virtual reality: a comprehensive research chart. Cyberpsychology, Behavior, and Social Networking, 17(6), 402-413.
26. Hoffman, H. G., Chambers, G. T., Meyer III, W. J., Arceneaux, L. L., Russel, W. J., Seibel, E. J., Richards, T. L., Sharar, S. R., Patterson, D. R. (2011). Virtual reality as an adjunctive non-pharmacologic analgesic for acute burn pain during medical procedures. Annals of Behavioral Medicine, 41(2), 183-191.
27. Hoffman H. G., Meyer III W. J., Ramirez M., Roberts L., Seibel E. J., Atzori B., Sharar S. R., and Patterson D. R. (2014). Feasibility of articulated arm mounted oculus rift virtual reality goggles for adjunctive pain control during occupational therapy in pediatric burn patients. Cyberpsychology, Behavior, and Social Networking, 17(6), 397-401.
28. Maani, C., Hoffman, H. G., DeSocio, P. A., (2008). Pain control during wound care for combat-related burn injuries using custom articulated arm mounted virtual reality goggles. Journal of CyberTherapy and Rehabilitation, 1:193-198.
29. Flores A., Hoffman H. G., Russell W., (2008). Longer, multiple virtual reality pain distraction treatments of Hispanic and Caucasian children with large severe burns. CyberTherapy Conference. San Diego, Calif.
30. Sharar, S. R., Carrougher, G. J., Nakamura, D., Hoffman, H. G., Blough, D. K., Patterson, D. R. (2007). Factors influencing the efficacy of virtual reality distraction analgesia during postburn physical therapy: preliminary results from 3 ongoing studies. Archives of Physical Medicine & Rehabilitation, 88(12), s43-s49.
31. Eccleston, C., Crombez, G. (1999). Pain demands attention: a cognitive-affective model of the interruptive function of pain. Psychological Bulletin, 125:356-366.
32. Hilgard, E. R. (1965). Hypnotic susceptibility. New York: Harcourt, Brace & World.
33. Hoffman H. G., Richards T. L., Bills A. R., (2006). Using FMRI to study the neural correlates of virtual reality analgesia. CNS Spectrums 11:45-51
34. Patterson, D. R.; Hoffman, H. G.; Palacios, A. Garcia; Jensen, M. J. (2006). Analgesic effects of posthypnotic suggestions and virtual reality distraction on thermal pain. Journal of Abnormal Psychology, Vol 115(4). 834-841.

35. Spiegel H., Aronson M., Fleiss J. L., Haber J. (1976). Psychometric analysis of the Hypnotic Induction Profile. *Int J Clin Exp Hypn.* 24(3):300-315
36. Hammond, C., Novian, A. (2014). The ISNR Comprehensive Bibliography of Neurofeedback in Scholarly Articles. Retrieved from: http://www.isnr.net/resources/comprehensive-bibliography.cfm
37. Lang E. V., Berbaum K. S., Faintuch S., Hatsiopoulou O., Halsey N., Li X., Berbaum M. L., Laser E., Baum J. (2006). Adjunctive self-hypnotic relaxation for outpatient medical procedures: a prospective randomized trial with women undergoing large core breast biopsy. *Pain.* 126(1-3):155-164
38. Lang E. V., Benotsch E. G., Fick L. J., Lutgendorf S., Berbaum M. L., Berbaum K. S., Logan H., Spiegel D. (2000). Adjunctive non-pharmacological analgesia for invasive medical procedures: a randomised trial. 355 (9214):1486-1490
39. Montgomery G. H., Bovbjerg D. H., Schnur J. B., David D., Goldfarb A., Weltz C. R., Schechter C., Graff-Zivin J., Tatrow K., Price D. D., Silverstein J. H. (2007). A randomized clinical trial of a brief hypnosis intervention to control side effects in breast surgery patients. J Natl Cancer Inst. 99(17):1304-1312
40. Lee J. S., Spiegel D., Kim S. B., Lee J. H., Kim S. I., Yang B. H., Choi J. H., Kho Y. C., Nam J. H. (2007). Fractal analysis of EEG in hypnosis and its relationship with hypnotizability. Int J Clin Exp Hypn. 55(1):14-31
41. Colgan S. M., Faragher E. B., Whorwell P. J. (1988). Controlled trial of hypnotherapy in relapse prevention of duodenal ulceration. Lancet. 1(8598):1299-1300
42. Lynn, S. J., Kirsch I., Barabasz A., Cardeña E., Patterson D. (2000). Hypnosis as an empirically supported clinical intervention: The state of the evidence and a look to the future. International Journal of Clinical and Experimental Hypnosis, 48(2), 239-59.
43. Lang, E. V., Benotsch E. G., Fick L. J., Lutgendorf S., Berbaum M. L., Berbaum K. S., Logan H., Spiegel D. (2000). Adjunctive non-pharmacological analgesia for invasive medical procedures: A randomised trial. Lancet, 355(9214), 1486-1490.
44. Ginandes, C., Brooks P., Sando W., Jones C., Aker J. (2003). Can medical hypnosis accelerate post-surgical wound healing? Results of a clinical trial. American Journal of Clinical Hypnosis, 45(4), 333-351.
45. Ginandes, C. S. & Rosenthal, D. I. (1999). Using hypnosis to accelerate the healing of bone fractures: A randomized controlled pilot study. Alternative Therapies in Health and Medicine, 5(2), 67-75.
46. Mehmet, C. O. (2000). About self-hypnosis and coronary artery bypass surgery. Journal of Cardiothoracic Surgery (Torino), 41(2), 335-336.
47. Peebles-Kleiger, M. J. (2000). The use of hypnosis in emergency medicine. Emergency Medicine Clinics of North America, 18(2), 327-338.
48. Gallagher, G., Rae, C. P., & Kinsella, J. (2000). Treatment of pain in severe burns. American Journal of Clinical Dermatology, 1(6), 329-335.
49. Spiegel, R. B. (2011). The Integration of Heart-Centered Hypnotherapy and Targeted Medical Hypnosis in the Surgical/Emergency Medicine Milieu. Journal of Heart-Centered Therapies, 14(2), 87-106.
50. Calipel, S., Lucaspolomeni, M., Wodey, E., & Ecoffey, C. (2005). Premedication in children: Hypnosis versus midazolam. Pediatric Anesthesia, 15(4), 275-281.
51. Butler, L. D., Symons, B. K., Henderson, S. L., Shortliffe, L. D., Spiegel, D. (2005). Hypnosis reduces distress and duration of an invasive medical procedure for children. Pediatrics, 115(1), e77-e85
52. Lobe, T. E. (2006). Perioperative hypnosis reduces hospitalization in patients undergoing the Nuss procedure for pectus excavatum. Journal of Laparoendoscopic & Advanced Surgical Techniques, 16(6), 639-642.
53. Cowan, G. S., Jr., et al. (2001). Assessment of the effects of a taped cognitive behavior message on postoperative complications (therapeutic suggestions under anesthesia). Obesity Surgery, 11(5), 589-593
54. Montgomery, G. H., Durham, K. N., & Redd, W. H. (2000). A meta-analysis of hypnotically induced analgesia: How effective is hypnosis? International Journal of Clinical and Experimental Hypnosis, 48, 138-153.
55. Patterson D. R., Jensen M. (2003). Hypnosis and clinical pain. Psychological Bulletin. 129(4):495-521.
56. Montgomery, G. H., David, D., Winkel, G., Silverstein, J. H., Bovbjerg, D. H. (2002). The Effectiveness of Adjunctive Hypnosis with Surgical Patients: A Meta-Analysis. Anesthesia & Analgesia. 94(6), 1639-1645.
57. Heap, M., Brown, R. J., Oakley, D. A. (2004). The Highly Hypnotizable Person: Theoretical, Experimental, and Clinical Issues. Psychology Press.
58. Hoeft, F., Gabrieli, J. D. E., Whitfield-Gabrieli, S., Haas, B. W., Bammer, R., Menon, V., Spiegel, D. (2012). Functional Brain Basis of Hypnotizability. Arch Gen Psychiatry. 69(10):1064-1072.
59. Vanhaudenhuyse A, Boly M, Balteau E, Schnakers C, Moonen G, Luxen A, Lamy M, Degueldre C, Brichant J F, Maquet P, Laureys S, Faymonville Me. (2009). Pain and non-pain processing during hypnosis: a thulium-YAG event-related fMRI study. *Neuroimage.* 47(3):1047-1054.
60. Gruzelier, J. (1998). a working model of the neurophysiology of hypnosis: a review of evidence. Contemporary Hypnosis, 15(1), 3-21
61. John H. Gruzelier (2006). Frontal functions, connectivity and neural efficiency underpinning hypnosis and hypnotic susceptibility. Contemp. Hypnosis, 23(1): 15-32.
62. McClain-Furmanski, D., Horton, J. E., & Crawford, H. J. (1999). Inhibition of pain: Effects on somatosensory event-related potentials during hypnotic analgesia in high but not low hypnotizable persons. Presented at Cognitive Neuroscience Society annual meeting, Washington, D.C.
63. Gruzelier J. H., Brow T. D., Perry A., Rhonder J., Thomas M. (1984). Hypnotic susceptibility: A lateral predisposition and altered cerebral asymmetry under hypnosis. International Journal of Psychophysiology; 2: 137-139.
64. McCormack K, Gruzelier J. H., (1993) Cerebral asymmetry and hypnosis: a signal detection analysis of divided visual field stimulation. Journal of Abnormal Psychology, 102: 352-7.
65. Jutai J., Gruzelier J. H., Golds J., Thomas M. (1993) Bilateral auditory-evoked potentials in conditions of hypnosis and focused attention. International Journal of Psychophysiology 15: 167-76.
66. Crawford H. J., Clarke S. W., Kitner-Triolo M. (1996). Self-generated happy and sad emotions in low and highly hypnotizable persons during waking and hypnosis: laterality and regional EEG activity differences. International Journal of Psychophysiology. 24(3):239-66.
67. Karlin, R., Morgan, D., & Goldstein, L. (1980). Hypnotic analgesia: A preliminary investigation of quantitated hemispheric electroencephalographic and attentional correlates. Journal of Abnormal Psychology, 89, 591-594.
68. Crawford, H. J., (1990). Cognitive and psychophysiological correlates of hypnosis. 47-54. In M. L. Fass & D.

Brown (Eds.), Creative mastery in hypnosis and hypnoanalysis: A festschrift for Erica Fromm. Hillsdale, N.J.: Lawrence Erlbaum Associates.
69. Gruzelier J. H. (1990): Neuropsychological investigations of hypnosis: Cerebral laterality and beyond. In *Hypnosis: Theory, Research and Clinical Practice*; Van Dyck R, Spinhoven Ph, Van der Does A J W, (eds) Free University Press: 38-51.
70. Tebecis A. K., Provins K A., Farnbach R. W., Pentony P. (1975). Hypnosis and the EEG. A quantitative investigation. J Nery Ment Dis. 161(1):1-17.
71. Graffin N. F., Ray W. J., Lundy R. (1995). EEG concomitants of hypnosis and hypnotic susceptibility. Journal of Abnormal Psychology. 104(1). 123-131.
72. Sabourin, M. E., Cutcomb, S. D., Crawford, H. J., Pribram, K. (1990). EEG correlates of hypnotic susceptibility and hypnotic trance: spectral analysis and coherence. International Journal of Psychophysiology. 10 (2). 125-142
73. Hammond, C. (2005). EEG Patterns and Hypnotizability. Biofeedback. 35-37.
74. Falkenstein M., Hohnbein J., Hoorman J., Blanke L. (1990). Effects of errors in choice reaction timetasks on the ERP under focussed and divided attention. Psychophysiological Brain Research. Tilburg: Tilburg University Press. 192-195.
75. Gehring W. J., Goss B., Coles M. G. H., Meyer D. E., Donchin E. A neural system for error detection and compensation. Psychological Science 1993; 4: 385-39.
76. Cardena E., Terhune D. (2009). A note of caution on the Waterloo-Stanford Group Scale of hypnotic susceptibility: a brief communication. Int J Clin Exp Hypn, 57(2): 222-6.
77. Baghdadi, G., Nasrabadi, A. M., (2012). Comparison of different EEG features in estimation of hypnosis susceptibility level. Computers in Biology and Medicine. 42(5), 590-597
78. Greenberg, R. P., Bornstein, R. F., Greenberg, M. D., & Fisher, S. (1992). A meta-analysis of antidepressant outcome under "blinder" conditions. Journal of Consulting and Clinical Psychology, 60(5), 664-669; discussion 670-677.
79. Greenberg, R. P., Bornstein, R. F., Zborowski, M. J., Fisher, S., & Greenberg, M. D. (1994). A meta-analysis of fluoxetine outcome in the treatment of depression. Journal of Nervous and Mental Disease, 182(10), 547-551.
80. Greenberg, R. P., & Fisher, S. (1989). Examining antidepressant effectiveness: Findings, ambiguities, and some vexing puzzles. Hillsdale, N.J.: Erlbaum.
81. Greenberg, R. P., & Fisher, S. (1997). Mood-mending medicines: Probing drug, psychotherapy, and placebo solutions. In S. Fisher & R. P. Greenberg (Eds.), From placebo to panacea: Putting psychiatric drugs to the test (pp. 115-172). New York: Wiley.
82. Kirsch, I., Moore, T. J., Scoboria, A., & Nicholls, S. S. (2002). The emperor's new drugs: An analysis of antidepressant medication data submitted to the U.S. Food and Drug Administration. Prevention & Treatment, 5(23).
83. Wagner, M. T., & Khanna, P. (1986). A neuropsychological model of hypnosis. International Journal of Psychosomatics, 33(3), 26-28.
84. Raz, A. (2007). Hypnobo: perspectives on hypnosis and placebo. American Journal of Clinical Psychology. 50(1), 29-36.
85. Amanzio, M. & Benedetti, F. (1999). Neuropharmacological dissection of placebo analgesia: Expectation-activated opioid systems versus conditioning-activated specific subsystems. The *Journal of Neuroscience,* 19(1), 484-494.
86. Bingel, U., Lorenz, J., Schoell, E., Weiller, C. & Büchel, C. (2006). Mechanisms of placebo analgesia: rACC recruitment of a subcortical antinociceptive network. *Pain,* 120(1-2), 8-15.
87. Vase, L., Petersen, G. L., Riley, J. L. & Price, D. D. (2009). Factors contributing to large analgesic effects in placebo mechanism studies conducted between 2002 and 2007. *Pain,* 145(1), 36-44.
88. Wager, T. D., Rilling, J. K., Smith, E. E., Sokolik, A., Casey, K. L., Davidson, R. J., Kosslyn, S. M., Rose, R. M., Cohen, J. D. (2004). Placebo-induced changes in fMRI in the anticipation and experience of pain. *Science,* 303(5661), 1162-1167.
89. Kirjanen, S. (2012). Brain activity during pain relief using hypnosis and placebo treatments: a literature review. Journal of European Psychology Students. Vol 3.
90. Benham, G., Bowers, S., Nash, M., & Muenchen, R. (1998). Self-fulfilling prophecy and hypnotic response are not the same thing. Journal of Personality and Social Psychology, 75(6), 1604-1613.
91. Kirsch, I., & Wickless, C. (1989). The effects of verbal and experiential expectancy manipulations on hypnotic susceptibility. Journal of Personality and Social Psychology, 57, 762-768.
92. Kirsch, I., Wickless, C., & Moffitt, K. H. (1999). Expectancy and suggestibility: Are the effects of environmental enhancement due to detection? International Journal of Clinical and Experimental Hypnosis, 47(1), 40-45.
93. Price, D. D., & Barrell, J. J. (2000). Mechanisms of analgesia produced by hypnosis and placebo suggestions. Progress in Brain Research, 122, 255-271.
94. Batty, M. J., Bonnington, S. Tang, B. K. Hawken, M. B. Gruzelier, J. H. (2006), Relaxation strategies and enhancement of hypnotic susceptibility: EEG neurofeedback, progressive muscle relaxation and self-hypnosis. Brain Research Bulletin, 71, 83-90.
95. Hammond, C. (1990). Handbook of Hypnotic Suggestions and Metaphors. The American Society of Clinical Hypnosis. New York: Norton and Company, Ltd.

What is claimed is:
1. A method for an interface of psychosomatic approaches and technology for effecting an immediate change of psychosomatic state and improving medical outcomes, the method comprising the steps of:
(a) using a plurality of biofeedback and neurofeedback sensors to continuously collect input data on a patient's psychosomatic state and using the input data to establish a baseline of real time physiological data;
(b) presenting a virtual reality (VR) immersive segment comprising a plurality of sensory experiences provided within a VR animated module to distract and disengage the patient's attentional resources from a current distressed state via immersion;
(c) combining guided biofeedback and neurofeedback training with hypnosis and guided response techniques facilitated by the VR animated module, to induce a relaxed state in the patient for a predetermined time period or until desired physiological markers are achieved, as measured by the biofeedback and neurofeedback sensors;
(d) determining from the input data if the patient is highly hypnotizable or low hypnotizable according to a predetermined threshold;

(e) guiding the patient verbally through either a hypnotic or guided suggestion session, depending on level of hypnotizability and measured brain activity, where the patient will be trained how to utilize attitudes and expectations to alter a psychosomatic state; and (f) whereby the patient will be able to achieve immediate alleviation of symptoms and/or change of distressed state regardless of the patient's abilities, distress level, health problem or associated medical treatment thus inducing immediate beneficial psychosomatic response, measurable health benefit, enhanced expectations and increased sense of self-efficacy.

2. The method as set forth in claim 1 wherein the step of (a) further comprises the steps of:

(a) collecting preliminary information from the patient and/or medical file for basic demographic and medical information, limitations and preferences for output visual and auditory segments;

(b) placing a plurality of sensors on the patient's scalp in order to obtain continuous data from a plurality of real time physiological markers and brain waves of the patient; and (c) comparing gathered input data with normative data and/or data from previous sessions of the patient to predetermine time and goals for the session.

3. The method as set forth in claim 1 wherein the step of (b) further comprises the steps of:

(a) providing the virtual reality (VR) segment comprising a combination of sensory, auditory and visual virtual experience including augmented reality, scent activators, and haptic technology;

(b) providing a brief time period for orientation in the VR segment, wherein the duration of the period for orientation will be determined by biofeedback (BFB) and neurofeedback (NFB) input data;

(c) terminating the segment automatically if the input data notably deteriorates within predetermined limits; and (d) allowing the segment to be prolonged or shortened by request of the patient or an operator.

4. The method as set forth in claim 1 wherein the step of (c) further comprises the steps of:

(a) presenting a VR interactive segment in a preselected VR environment that will reflect visually the measures of the patient's current physiological state as the segments are a visual manifestation of BFB and NFB input data corresponding to the patient physiological markers;

(b) guiding via a voice or with subtitles for the auditory impaired the patient into a relaxed state;

(d) introducing interactive and engaging animated images in the VR environment that will move by reflecting the changes in the patient's physiological markers using BFB/NFB training principles;

(c) switching to an automatic mode of improving the condition in the VR environment with a proper guidance for relaxation if the patient is not successful within a predetermined time period to start interacting with the images;

(d) resuming the interactive VR environment if the markers improve compared to baseline within a predetermined time period and proceeding to the next predetermined stage for a gradual completion of a session; and (e) terminating the session automatically if the BFB and NFB input data deteriorates over a predetermined margin thereby emitting an indicating signal to an operator.

5. The method as set forth in claim 4 wherein subtitles are provided where guiding and directions are needed due to hearing impairment of the patient.

6. The method as set forth in claim 1 wherein the step of (d) further comprises the steps of:

(a) making a statement and/or a visual summary for trance/experience ratification affirmatively indicating the patient's ability to influence his/her own body by will as demonstrated in a previous phase;

(b) presenting a 3D VR segment of a generic body image with predetermined specifications for location, medical problem and/or medical procedure associated with a treatment;

(c) conducting a hypnotic induction for the patient with high hypnotizability and while in a trance, instructing the patient on how to alter the patient's body's state, using the patient's mind, in a manner demonstrated by animation in the body image thereby indicating an achievement of a predetermined goal;

(d) providing a posthypnotic suggestion about any desired changes, behavior and/or abilities the patient may want or need to achieve;

(e) conducting guided animated demonstration in the virtual body for the patient with low hypnotizability while in a relaxed state, to teach the patient what the patient can accomplish by will in the patient's own body in order to achieve the desired outcome;

(f) offering an affirmative statement demonstrated with a visual summary of the patient's ability to change and improve the patient's current state;

(g) determining if physiological markers are more distressed over a predetermined threshold and consequently shortening the demonstration to an achieved goal; and (h) concluding the session by returning to a VR relaxation segment from a relaxed state with an affirmative statement or image.

7. The method as set forth in claim 1 wherein the VR animated modules comprise either one or a combination selected from a group consisting of a visual module, an auditory module, and a memory module.

8. The method as set forth in claim 7 wherein the auditory module further comprises embedding binaural beats, wherein individual tones are presented to each ear of the patient providing effective stimulus for brainwave training.

9. The method as set forth in claim 8 wherein the auditory module further comprises imbedding double induction in verbal directive/inductive messages wherein playing two messages, at the same time, to separate ears making the patient more susceptible to the messages.

10. The method as set forth in claim 7 wherein the visual module further comprises embedding subliminal messaging in the VR visual content wherein short and rapid messages or words are played to the patient whereby making the patient more susceptible to the messages.

11. The method as set forth in claim 1 wherein the guiding steps are conducted without verbal directions and solely as VR immersive distracting/disengaging steps utilizing the visual segments.

12. The method as set forth in claim 1 wherein the method further includes the step of providing a storing means comprising a software program for recording and storing all activity in a session including but not limited to the baseline data, the input data, output data, timing, most effective data segments, length and type of segments, and their sequential order, wherein the software program further provides a full audit trail of every session.

\* \* \* \* \*